United States Patent
Hete et al.

[11] Patent Number: 6,123,074
[45] Date of Patent: *Sep. 26, 2000

[54] OXYGEN MIXING IN A BLOWER-BASED VENTILATOR

[75] Inventors: Bernie F. Hete, Trafford; James D. Srock, Valencia, both of Pa.

[73] Assignee: Respironics, Inc., Pittsburgh, Pa.

[ * ] Notice: This patent is subject to a terminal disclaimer.

[21] Appl. No.: 08/899,432

[22] Filed: Jul. 24, 1997

Related U.S. Application Data

[63] Continuation of application No. 08/707,185, Sep. 3, 1996, Pat. No. 5,701,883.

[51] Int. Cl.$^7$ ............... A62B 7/00; A62B 9/00; G05B 1/00
[52] U.S. Cl. ............... 128/205.11; 128/203.14; 128/203.25; 128/204.21; 128/204.26
[58] Field of Search ............... 128/203.14, 203.22, 128/203.25, 204.21, 204.23, 204.26, 205.11

[56] References Cited

U.S. PATENT DOCUMENTS

| | | | |
|---|---|---|---|
| 3,727,627 | 4/1973 | Bird et al. | 137/100 |
| 3,895,642 | 7/1975 | Bird et al. | 137/7 |
| 4,022,234 | 5/1977 | Dobritz | 137/88 |
| 4,023,587 | 5/1977 | Dobritz | 137/88 |
| 4,587,967 | 5/1986 | Chu et al. | 128/204.21 |
| 4,838,257 | 6/1989 | Hatch | 128/204.18 |
| 5,148,802 | 9/1992 | Sanders et al. | 128/204.18 |
| 5,158,584 | 10/1992 | Tamura | 55/158 |
| 5,161,525 | 11/1992 | Kimm et al. | 128/204.26 |
| 5,239,995 | 8/1993 | Estes et al. | 128/204.23 |
| 5,265,594 | 11/1993 | Olsson et al. | 128/204.18 |
| 5,271,389 | 12/1993 | Isaza et al. | 128/204.21 |
| 5,299,568 | 4/1994 | Forare et al. | 128/205.11 |
| 5,303,698 | 4/1994 | Tobia et al. | 128/204.21 |
| 5,313,937 | 5/1994 | Zdrojkowski | 128/202.22 |
| 5,315,989 | 5/1994 | Tobia | 128/204.28 |
| 5,433,193 | 7/1995 | Sanders et al. | 128/204.18 |
| 5,452,714 | 9/1995 | Anderson et al. | 128/205.11 |
| 5,535,738 | 7/1996 | Estes et al. | 128/204.23 |
| 5,540,220 | 7/1996 | Gropper et al. | 128/204.23 |
| 5,582,163 | 12/1996 | Bonassa | 128/204.18 |
| 5,632,270 | 5/1997 | O'Mahony et al. | 128/204.24 |
| 5,664,560 | 9/1997 | Merrick et al. | 128/203.25 |
| 5,692,497 | 12/1997 | Schnitzer et al. | 128/204.21 |
| 5,701,883 | 12/1997 | Hete et al. | 128/204.26 |
| 5,797,393 | 8/1998 | Kohl | 128/204.23 |

OTHER PUBLICATIONS

Mott, Robert Applied Fluid Mechanics, Chapter 4, May 1974.

*Primary Examiner*—John G. Weiss
*Assistant Examiner*—Joseph Weiss
*Attorney, Agent, or Firm*—Michael W. Haas

[57] ABSTRACT

An oxygen mixing arrangement for or in a pressure support ventilator, in which a modular oxygen-providing assembly is selectively insertable into a greater respiration apparatus. Mixing accuracy and controllability is maintained by using gas supplies that have a wide range of pressures. Further, oxygen leakage is minimized by connecting the modular oxygen-providing assembly at a point of the respiration circuit of the greater respiration apparatus that is downstream from a valving arrangement normally used for venting patient exhaust flow and for controlling system pressure by venting excess gas flow to the ambient atmosphere.

12 Claims, 17 Drawing Sheets

OXYGEN MIXING IN A BLOWER-BASED VENTILATOR

This application is a continuation of application Ser. No. 08/707,185, filed on Sep. 3, 1996, now issued U.S. Pat. No. 5,701,883, the contents of which are hereby incorporated by reference.

FIELD OF THE INVENTION

The present invention generally relates to ventilator systems, such as pressure support ventilators, and valve arrangements for use therewith or therefor, and more particularly, to oxygen mixing arrangements for and in such pressure support ventilators.

BACKGROUND OF THE INVENTION

Historically, many individuals have required the use of pressure support ventilators in order to assist with respiratory problems, such as sleep apnea. Thus, over the years, a wide range of pressure support ventilators have been developed and produced that are designed to meet the needs of the individuals in question.

Essentially, the primary objective of a pressure support ventilator is to impart to a respiratory patient sufficient air (or gas) pressure in his or her airway so as to either preliminarily obviate the effect of any resistances or impedances within the patient's airway that might otherwise arise in the context of a patient's normal breathing patterns (e.g. sleep apnea) or even overcome airway resistances or impedances that might be of a more static nature (e.g. longer-term constrictions of the airway, or even lungs, caused by any of a number of possible physiological factors). As briefly discussed below, this impartation of pressure to a patient's airway has taken different forms over the years.

One basic form of pressure support that was developed initially was a so-called "continuous positive airway pressure", or "CPAP" support system, including those systems developed by Respironics, Inc., of Murrysville, Pa. This would involve the provision essentially of one constant pressure throughout a patient's entire breathing pattern. Although the single constant pressure was normally sufficient to overcome a patient's airway resistances or impedances (as discussed above), it was often found that a patient's ability to effectively exhale in such a context might be difficult.

An innovation over the above-described "CPAP", as developed by Respironics, Inc., was what was regarded as a "bi-level" support system and is implemented in the Respironics BiPAP® devices. This involved the provision of suitable sensing components for detecting the periods of time during which a patient would either inhale or exhale. Consequently, the sensing components were utilized in such a way that, during inhalation, one given pressure could be provided to the patient, while during exhalation, another, notably reduced, pressure could be provided. Several U.S. patents describe this "bi-level" system in detail, including U.S. Pat. Nos. 5,433,193; 5,313,937; 5,239,995; and 5,148,802, all of which are hereby expressly incorporated by reference as if set forth in its entirety herein.

In further innovations, apparatus and methods were developed in which the air or gas pressure supplied to a patient in the context of a pressure support system could be variable, either depending on a preprogrammed algorithm that exacted a predetermined time-dependent pattern of pressures on the patient or specific, instantaneously monitored demands of the patient. A device along these lines is disclosed in U.S. Pat. No. 5,535,738, which is also hereby expressly incorporated by reference as if set forth in its entirety herein.

Generally, whether the pressure administered to a patient is intended to be virtually constant over given periods of time (as in a "BiPAP" system) or variable, there has typically been a need to monitor the pressure being provided to the patient with a feedback control system so that, if necessary, the pressure can be readjusted so as to conform to the desired output pressure. Typically, such feedback control has not involved adjustment of the blower motor, as there are logistical problems associated with this (such as imprecisions in changing the motor speed within a short period of time, for instance). Accordingly, many conventional systems have included a single pressure relief valve, situated between the blower outlet and the start of the "patient circuit" (i.e. that portion of the respiratory circuit that includes tubing, filters, water traps, valves, etc. that are regarded as being necessary for providing suitably conditioned air or gas to the patient in question), that serves to readjust the air or gas pressure in the respirator circuit in response to prompts from the feedback control system. Such a pressure relief valve would also be typically used for exhausting air and/or gas emanating from a patient upon exhaling (thereby causing a net "negative" flow in the respirator circuit, i.e. back towards the blower, which would be vented off through the pressure relief valve).

Because such pressure relief valves are typically embodied by proportional valves that open to merely vent a portion of the flow of the respirator circuit to the ambient atmosphere (or other predetermined remote location), it is essentially the case that they are only able to increase pressure within the system upon being further closed from an already open position, wherein a fully "open" position would result in maximum venting from the system (thereby resulting in decreased pressure in the patient circuit) and a fully "closed" position would result in minimal or nonexistent venting from the system (thereby resulting in increased pressure in the patient circuit).

Because, especially in the context of respiratory patients who may require increased airway pressure from time to time, it must often be assumed that an allowance must be made for increasing the pressure provided to the patient from a lower level, it was therefore often necessary, in the context of systems utilizing a pressure relief valve as discussed above, to keep the valve open during normal inhalations and exhalations of the patient, with the understanding that a sudden, instantaneous demand for greater pressure (as initiated, for example, by an unexpectedly occurring blockage or constriction in the patient's airway and as measured by appropriate pressure and/or flow sensors at the patient circuit), could be attended to by closing the pressure relief valve to the degree sufficient for providing the demanded pressure. Alternatively, and especially in the context of more continuous systems such as the "BiPAP", it would often merely be the case that a wide range of constant inhalation pressures (as provided by the system) had to be allowed for in manufacturing the systems in question, in view of their use among a wide variety of patients with widely varying static pressure requirements. In any case, in order to assure a sufficient margin of safety, there was often the consequence that tremendous levels of air or gas flow would be vented away by the pressure relief valve, to be "reined in" only in those instances where greater pressure (for the patient) would be required.

Thus, although the use of a single pressure relief valve, as discussed above, can offer stable, fast open-loop pressure control, its utility has been limited by the level of pressure and flow required from the blower fan, which itself has not been, and essentially cannot be, used for pressure control. High motor speeds in this context have the tendency of increasing bearing and motor loads (in proportion to the square of motor speed), while the resultant excessive flow has the tendency of wasting power since work needs to be done to the fluid to bring it up to pressure, only to release it to the atmosphere. It stands to note that the exhausting of large gas flows also tends to be very noisy.

Recent years have also seen the development of, and demands for, blower-based pressure support ventilators that provide considerably larger pressures than conventional devices. Since this would normally result in the provision of ventilators having blowers that would subsequently provide astronomically excessive levels of flow that, in the context of single pressure-relief valve arrangements as discussed above, would result in tremendous wasted flow and unprecedentedly excessive noise levels (from exhaust), a need has arisen to efficiently regulate respirator flow and pressure in a manner that minimizes waste while still providing the patient with adequate respiratory support.

Another perennial challenge in the context of pressure-support ventilators is found in that historically, many individuals, including patients with given types of lung disease, have required not only general pressure-support respiratory assistance but also additional assistance in the form of elevated concentrations of oxygen, with the objective of maintaining proper levels of oxygen in the arteries. Consequently, the pressure-support ventilators that have been developed over the years, such as those discussed in the U.S. patents cited further above, have concomitantly placed demands on the manner in which arrangements for providing supplemental oxygen can be incorporated into the ventilators.

To this end, various methods of "oxygen mixing" have been developed with varying degrees of success. In at least one known realization, involving blower-based, non-invasive ventilators, supplemental oxygen is effectively "bled" into the individual's airstream in the immediate vicinity of the mask worn by the individual being treated. However, such known arrangements have tended to utilize continuous oxygen flows through the mask, with the undesirable result that a considerable quantity of oxygen may be wasted and continues to flow whether the individual is inhaling or exhaling. Additionally, the concentration of oxygen in the inspired air is unknown, thus inhibiting the ability of a clinician to control such treatment. Further, there is a concomitant danger in the possible effects of inadvertently venting oxygen directly into the atmosphere, either via excessive oxygen flow that leaves the vicinity of the individual's mask or through other leaks in the system, or even into the interior of a respirator apparatus, where the vented or leaked oxygen might interact with high temperatures within the unit and invite the risk of combustion.

A need has therefore arisen in conjunction with the provision of an oxygen mixer that accurately provides individuals with a known and accurately predetermined quantity of supplemental oxygen in a ventilator device such as a pressure support ventilator.

SUMMARY OF THE INVENTION

In accordance with at least one preferred embodiment of the present invention, an oxygen mixing arrangement is provided that minimizes the quantity of wasted oxygen, that maintains pressure stability that provides a safe environment for mixing oxygen, that affords the provision of an oxygen blending system as an accessory "module" and that maintains mixing accuracy and controllability by using gas supplies that have a wide range of pressures.

In one embodiment of the present invention, the minimization of excess flow (i.e. venting) of oxygen is achieved by injecting the oxygen into the general airflow of the respirator apparatus at a point downstream from any pressure relief valve or other components capable of venting air and/or gas into the ambient atmosphere. Thus, as long as there is a net flow of air and/or gas towards the patient circuit, there will not be any direct, deliberate venting of the oxygen to the atmosphere through such a valve or valves. In the presence of negative airflow, i.e. back from the patient circuit towards the blower, suitable controls can temporarily shut off the oxygen supply so as to prevent the direct, deliberate flow of oxygen from the point at which it is admitted into the general respirator circuit towards any pressure relief valving arrangement. As a result, essentially the only venting of oxygen that might occur would be that conventionally associated with leakage in the patient circuit and that associated with a negative gas flow (i.e. away from the patient), containing oxygen that has already been injected into the system in the presence of a positive gas flow (i.e. towards the patient), that is unavoidably exhausted to the ambient atmosphere through the pressure relief valving arrangement or other exhaust arrangement provided for the very purpose of exhausting such negative gas flow. In both cases, the loss of oxygen is normally very low and thus considered to be acceptable.

In summary, one aspect of the present invention broadly contemplates apparatus for delivering pressurized gas to the airway of a patient, the apparatus comprising:

a gas flow generator arrangement for providing a flow of the gas;

a conduit arrangement for delivery of the gas flow to the airway of the patient;

the conduit arrangement comprising at least one primary conduit portion for carrying a primary flow of the gas towards the airway of the patient;

an arrangement for providing supplemental oxygen to the patient concomitantly with the provision of the primary flow of the gas to the patient;

the arrangement for providing supplemental oxygen comprising:

an arrangement for introducing a flow of supplemental oxygen into the at least one primary conduit portion of the apparatus;

an arrangement for metering the flow of supplemental oxygen into the at least one primary conduit portion of the apparatus;

the metering arrangement comprising an arrangement for regulating the flow of supplemental oxygen into the at least one primary conduit portion of the apparatus as a function of at least one of:

the magnitude of the primary flow in the at least one main conduit portion; and the direction of the primary flow in the at least one main conduit portion.

In another aspect, the present invention broadly contemplates a method of controlling the pressure of gas flow delivered to the airway of a patient in apparatus for delivering pressurized gas to the airway of a patient, such apparatus comprising a gas flow generator arrangement for providing a flow of gas and a conduit arrangement for delivery of the gas flow to the airway of the patient; the method comprising the steps of:

carrying, in the conduit means, a primary flow of the gas towards the airway of the patient;

providing supplemental oxygen to the patient concomitantly with the provision of the primary flow of the gas to the patient;

the step of providing supplemental oxygen comprising the steps of:

introducing a flow of supplemental oxygen into the at least one primary conduit portion of the apparatus;

metering the flow of supplemental oxygen into the at least one primary conduit portion of the apparatus;

the metering step comprising the step of regulating the flow of supplemental oxygen into the at least one primary conduit portion of the apparatus as a function of at least one of:

the magnitude of said primary flow in the at least one main conduit portion; and the direction of the primary flow in the at least one main conduit portion.

In accordance with at least one preferred embodiment of the present invention, an arrangement is contemplated in which blower output can be controlled in such a manner that the desired levels of pressure are still able to be provided, without wasting blower output flow.

In accordance with a preferred embodiment of the present invention, a first valve is provided that serves to restrict blower flow, without venting the same from the system, along with a second valve for relieving pressure as needed.

In accordance with a preferred embodiment of the present invention, the pressure and flow are adjustable as they have been previously, with the added advantage that the aforementioned first valve is also continuously and proportionally adjustable in such a manner that, upon a demand being placed on the system for increased flow, the blower output curve will be shifted so as to result in minimal excess flow in response to the pressure also simultaneously demanded.

In summary, one aspect of the present invention broadly contemplates apparatus for delivering pressurized gas to the airway of a patient, the apparatus comprising:

a gas flow generator arrangement for providing a flow of the gas;

a conduit arrangement for delivery of the gas flow to the airway of the patient;

an arrangement for controlling the pressure of the gas flow delivered to the airway of the patient;

the controlling arrangement comprising:

an arrangement for restricting the gas flow in the conduit arrangement prior to its being delivered to the airway of the patient;

an arrangement for selectively venting a portion of the gas flow away from the conduit arrangement prior to its being delivered to the airway of the patient; and an arrangement for selectively actuating the restricting arrangement and the venting arrangement in a manner to substantially minimize the quantity of gas flow vented away from the conduit arrangement prior to its being delivered to the airway of the patient.

In another aspect, the present invention broadly contemplates, in apparatus for delivering pressurized gas to the airway of a patient, such apparatus comprising a gas flow generator arrangement for providing a flow of the gas and a conduit arrangement for delivery of the gas flow to the airway of the patient; an arrangement for controlling the pressure of the gas flow delivered to the airway of the patient, the controlling arrangement comprising:

an arrangement for restricting the gas flow in the conduit arrangement prior to its being delivered to the airway of the patient;

an arrangement for selectively venting a portion of the gas flow away from the conduit arrangement prior to its being delivered to the airway of the patient; and an arrangement for selectively actuating the restricting arrangement and the venting arrangement in a manner to substantially minimize the quantity of gas flow vented away from the conduit arrangement prior to its being delivered to the airway of the patient.

In yet another aspect, the present invention broadly contemplates a method of controlling the pressure of gas flow delivered to the airway of a patient in apparatus for delivering pressurized gas to the airway of a patient, such apparatus comprising a gas flow generator arrangement for providing a flow of the gas and a conduit arrangement for delivery of the gas flow to the airway of the patient; the method comprising the steps of:

restricting the gas flow in the conduit arrangement prior to its being delivered to the airway of the patient;

selectively venting a portion of the gas flow away from the conduit arrangement prior to its being delivered to the airway of the patient; and selectively actuating the restricting arrangement and the venting arrangement in a manner to substantially minimize the quantity of gas flow vented away from the conduit arrangement prior to its being delivered to the airway of the patient.

BRIEF DESCRIPTION OF THE DRAWINGS

The present invention and its presently preferred embodiments will be better understood by way of reference to the detailed disclosure herebelow and to the accompanying drawings, wherein.

DETAILED DESCRIPTION OF THE PREFERRED EMBODIMENTS

Figure 1:
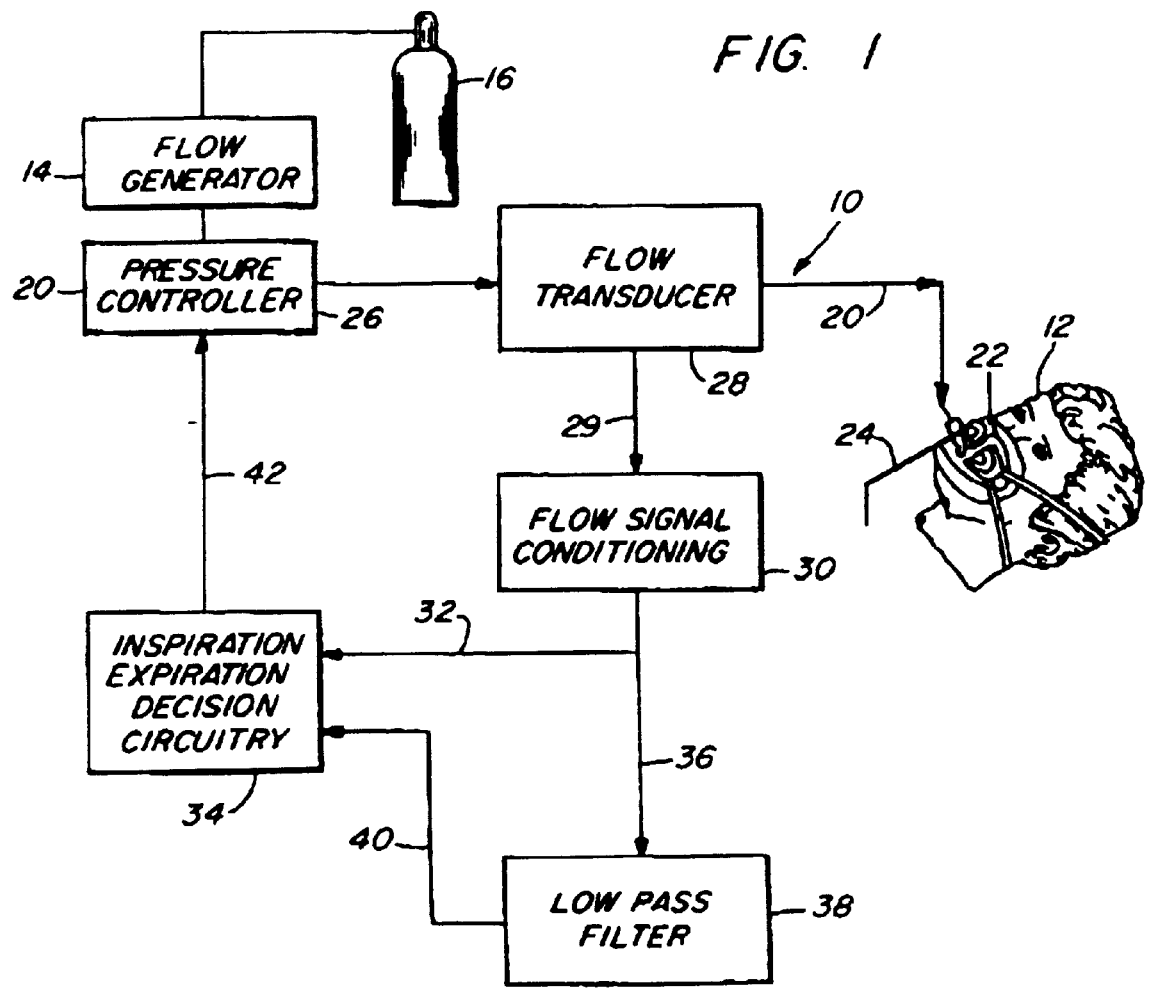
FIG. 1 is a functional block diagram of a conventional apparatus having components, and being operable by at least portions of a method, that may be utilized in accordance with the embodiments of the present invention.
Figure 2:
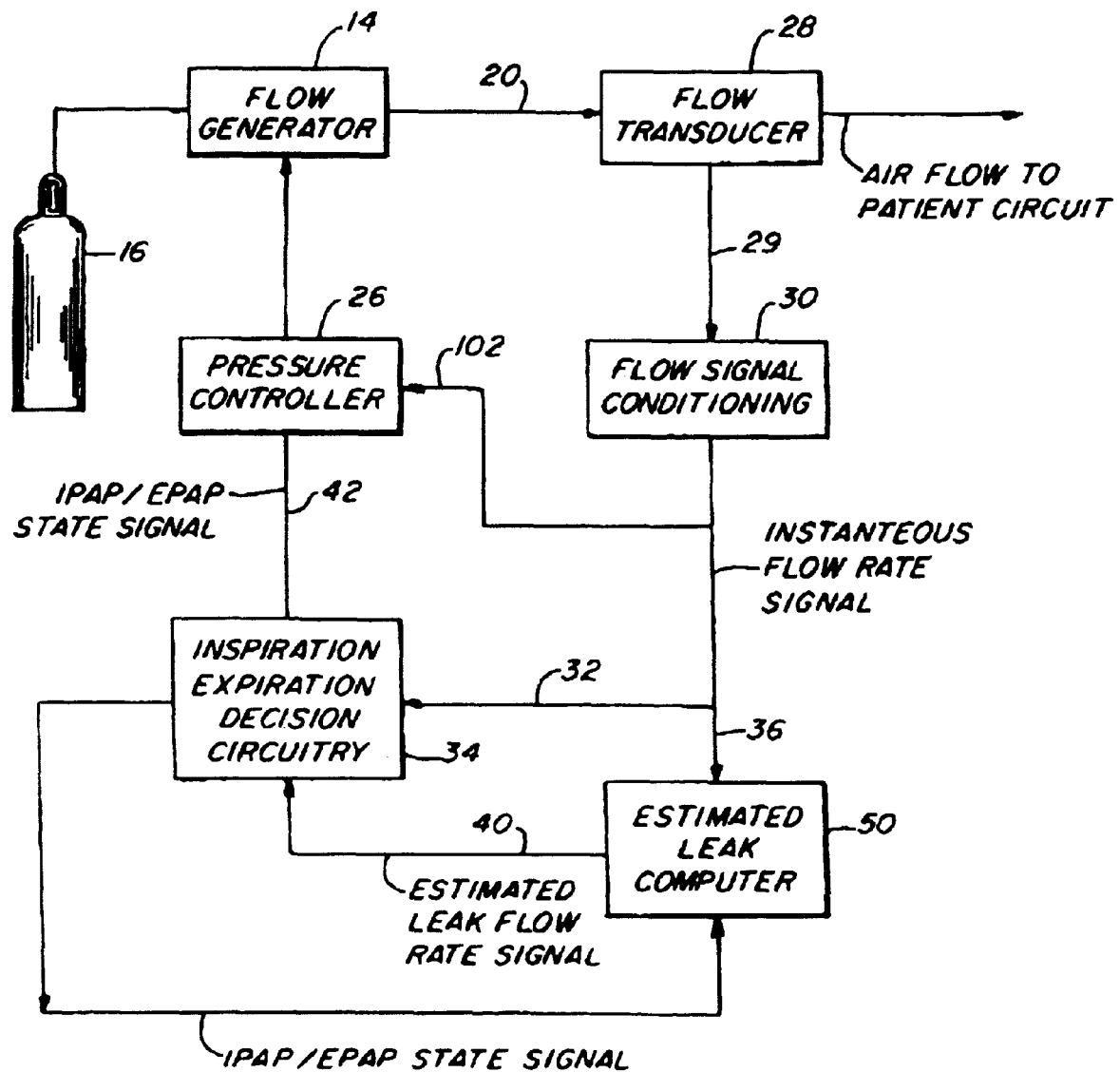
FIG. 2 is a functional block diagram showing an alternative embodiment.
Figure 3:
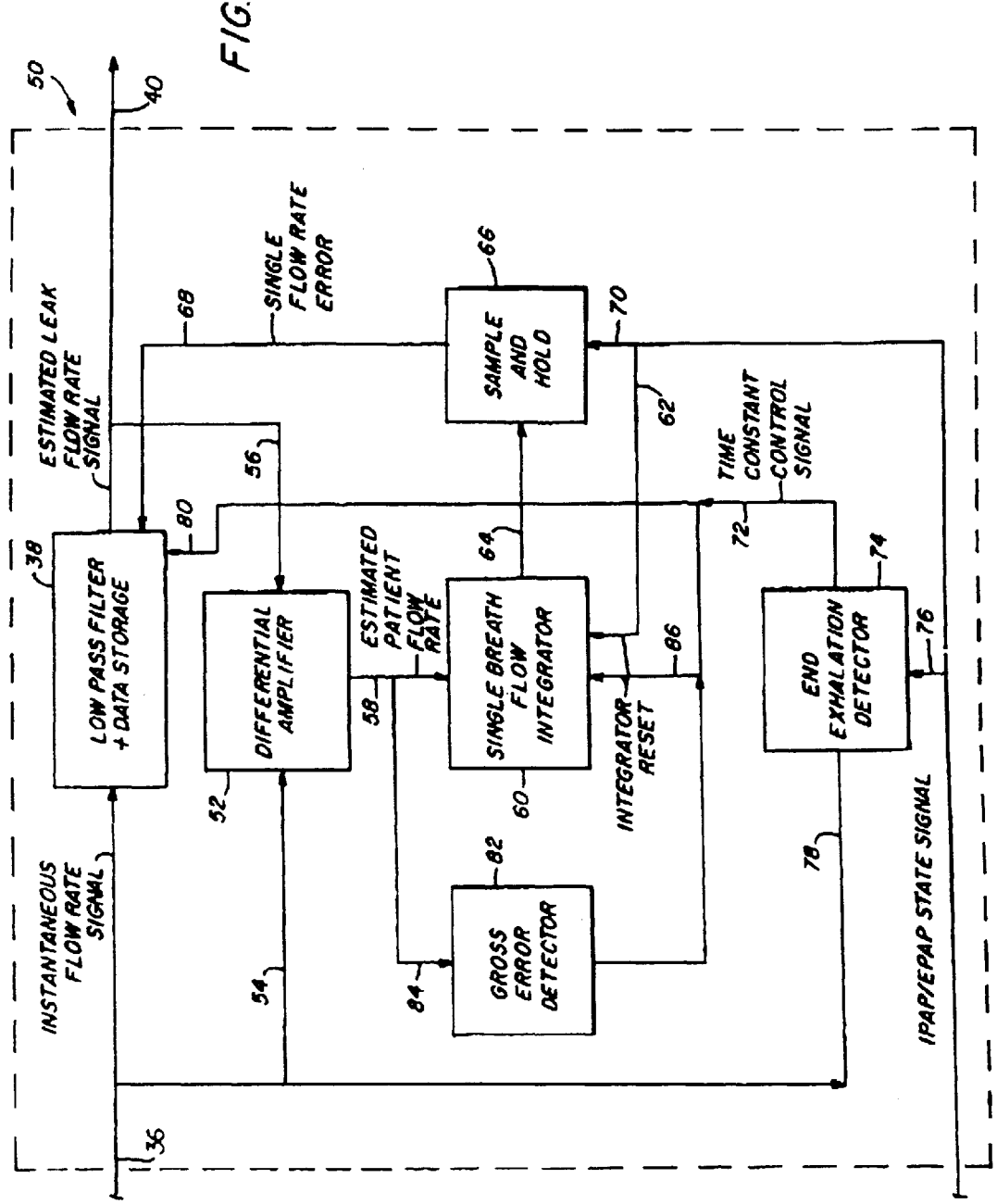
FIG. 3 is a functional block diagram of the Estimated Leak Computer of FIG. 2.

The disclosure presently will turn to a description of a conventional bi-level apparatus, as illustrated in FIGS. 1–3, that possesses components, and contemplates manipulations of the same, that may be utilized in accordance with at least one presently preferred embodiment of the present invention. Other details regarding such conventional apparatus may be found in the U.S. Patents listed at the beginning of this specification, especially U.S. Pat. No. 5,148,802. It is to be understood that the conventional bi-level apparatus described and illustrated with respect to FIGS. 1–3 is provided as an example and is in no way meant to limit the spirit and scope of the invention.

Apparatus 10 in FIG. 1 is operable according to a process for delivering breathing gas, such as air, alternately at relatively higher and lower pressures (i.e., equal to or above ambient atmospheric pressure) to a patient 12 for treatment of a given respiratory condition, such as the condition known as sleep apnea.

Apparatus 10 comprises a gas flow generator 14 (e.g., a blower) which receives breathing gas from any suitable source, such as a pressurized bottle 16 or the ambient atmosphere, for example. The gas flow from flow generator 14 (which, for all intents and purposes, can be considered to be a pressure generator) is passed via a delivery conduit 20 to a breathing appliance such as a mask 22 of any suitable known construction which is worn by patient 12. The mask 22 may preferably be a nasal mask or a full face mask 22 as shown. Other breathing appliances which may be used in lieu of a mask include nasal cannulae, an endotracheal tube, or any other suitable appliance for interfacing between a source of breathing gas and a patient, consistent with the desired effect to be achieved through use of the apparatus 10.

The mask 22 includes a suitable exhaust port means, schematically indicated at 24, for exhaust of breathing gases during expiration. Exhaust port 24 preferably is a continuously open port which imposes a suitable flow resistance upon exhaust gas flow to permit a pressure controller 26, located in line with conduit 20 between flow generator 14 and mask 22, to control the pressure of air flow within conduit 20 and thus within the airway of the patient 12. The flow via exhaust port 24 is one component, and typically the major component of the overall system leakage, which is an important parameter of system operation. In an alternative embodiment to be discussed hereinbelow, it has been found that a non-rebreathing valve may be substituted for the continuously open port 24.

The pressure controller 26 is operative to control the pressure of breathing gas within the conduit 20 and thus within the airway of the patient. Pressure controller 26 is located downstream of flow generator 14 and may take the form of an adjustable valve which provides a flow path which is open to the ambient atmosphere via a restricted opening, the valve being adjustable to maintain a constant pressure drop across the opening for all flow rates and thus a constant pressure within conduit 20.

Also interposed in line with conduit 20, downstream of pressure controller 26, is a suitable flow transducer 28 that generates an output signal that is fed, as indicated at 29, to a flow signal conditioning circuit 30 for derivation of a signal 35 proportional to the instantaneous flow rate of breathing gas within conduit 20 to the patient.

It will be appreciated that flow generator 14 is not necessarily a positive displacement device. It may be, for example, a blower which creates a pressure head within conduit 20 and provides air flow only to the extent required to maintain that pressure head in the presence of patient breathing cycles, the exhaust opening 24, and action of pressure controller 26 as above described. Accordingly, when the patient is exhaling, peak exhalation flow rates from the lungs may far exceed the flow capacity of exhaust port 24. As a result, exhalation gas backflows within conduit 20 through flow transducer 28 and toward pressure controller 26, and the instantaneous flow rate signal from transducer 28 thus will vary widely within a range from relatively large positive (i.e. toward the patient) flow to relatively large negative (i.e. from the patient) flow.

The instantaneous flow rate signal from flow signal conditioning circuitry 30 is fed, as indicated at 32, to a decision module 34, a known comparator circuit for example, and is additionally fed, as indicated at 36, to a low pass filter 38. Low pass filter 38 has a cut-off frequency low enough to remove from the instantaneous flow rate input signal most variations in the signal which are due to normal breathing. Low pass filter 38 also has a long enough time constant to ensure that spurious signals, aberrant flow patterns and peak instantaneous flow rate values will not dramatically affect system average flow. That is, the time constant of low pass filter 38 is selected to be long enough that it responds slowly to the instantaneous flow rate signal input. Accordingly, most instantaneous flow rate input signals which could have a large impact on system average flow in the short term have a much smaller impact over a longer term, largely because such instantaneous flow rate signal components will tend to cancel over the longer term. For example, peak instantaneous flow rate values will tend to be alternating relatively large positive and negative flow values corresponding to peak inhalation and exhalation flow achieved by the patient during normal spontaneous breathing. The output of low pass filter 38 thus is a signal which is proportional to the average flow in the system, and this is typically a positive flow which corresponds to average system leakage (including flow from exhaust 24) since, as noted, inhalation and exhalation flow cancel for all practical purposes.

The average flow signal output from the low pass filter 38 is fed as indicated at 40 to decision circuitry 34 where the instantaneous flow rate signal is continually compared to the system average flow signal. The output of the decision circuitry 34 is fed as a drive signal indicated at 42 to control the pressure controller 26. The pressure magnitude of breathing gas within conduit 20 thus is coordinated with the spontaneous breathing effort of the patient 12, as follows.

When the patient begins to inhale, the instantaneous flow rate signal goes to a positive value above the positive average flow signal value. Detection of this increase in decision circuitry 34 is sensed as the start of patient inhalation. The output signal from decision circuitry 34 is fed to pressure controller 26 which, in response, provides higher pressure gas flow within conduit 20 and thus higher pressure within the airway of the patient 12. This is the higher magnitude pressure value of our bi-level CPAP system and is referred to hereinbelow as IPAP (inhalation positive airway pressure). During inhalation, the flow rate within conduit 20 will increase to a maximum and then decrease as inhalation comes to an end.

At the start of exhalation, air flow into the patient's lungs is nil and as a result the instantaneous flow rate signal will be less than the average flow rate signal which, as noted is a relatively constant positive flow value. The decision circuitry 34 senses this condition as the start of exhalation and provides a drive signal to pressure controller 26 which, in response, provides gas flow within conduit 20 at a lower pressure which is the lower magnitude pressure value of the bi-level CPAP system, referred to hereinbelow as EPAP (exhalation positive airway pressure). As has been noted hereinabove the range of EPAP pressures may include ambient atmospheric pressure. When the patient again begins spontaneous inhalation, the instantaneous flow rate signal again increases over the average flow rate signal, and the decision circuitry once again feeds a drive signal to pressure controller 26 to reinstitute the IPAP pressure.

System operation as above specified requires at least periodic comparison of the input signals 32 and 40 by decision circuitry 34. Where this or other operations are described herein as continual, the scope of meaning to be ascribed includes both continuous (i.e. uninterrupted) and periodic (i.e. at discrete intervals).

As has been noted, the system 10 has a built-in leakage via exhaust port 24 thus assuring that the average flow signal will be at least a small positive flow. During inhalation, the flow sensed by the flow transducer will be the sum of exhaust flow via port 24 and all other system leakage downstream of transducer 28, and inhalation flow within the airway of the patient 12. Accordingly, during inhalation the instantaneous flow rate signal as conditioned by conditioning module 30, will reliably and consistently reflect inhalation flow exceeding the average flow rate signal. During exhalation flow from the lungs of the patient far exceeds the flow capacity of exhaust port 24. Accordingly, exhalation air backflows within conduit 20 past transducer 28 and toward pressure controller 26. Since pressure controller 26 is operable to maintain set pressure, it will act in response to flow coming from both the patient and the flow generator to open an outlet port sufficiently to accommodate the additional flow volume and thereby maintain the specified set pressure as determined by action of decision circuitry 34.

In both the inhalation and exhalation cycle phases, the pressure of the gas within conduit 20 exerts a pressure within the airway of the patient to maintain an open airway and thereby alleviate airway constriction.

In practice, it may be desirable to provide a slight offset in the switching level within decision circuitry 34 with respect to the average flow rate signal, so that the system does not prematurely switch from the low pressure exhalation mode to the higher pressure inhalation mode. That is, a switching setpoint offset in the positive direction from system average flow may be provided such that the system will not switch to the IPAP mode until the patient actually exerts a significant spontaneous respiratory effort of a minimum predetermined magnitude. This will ensure that the initiation of inhalation is completely spontaneous and not forced by an artificial increase in airway pressure. A similar switching setpoint offset may be provided when in the IPAP mode to ensure the transition to the lower pressure EPAP mode will occur before the flow rate of air into the lungs of the patient reaches zero (i.e. the switch to EPAP occurs slightly before the patient ceases inhalation.) This will ensure that the patient will encounter no undue initial resistance to spontaneous exhalation.

From the above description, it will be seen that a method of treating sleep apnea is provided according to which the airway pressure of the patient is maintained at a higher positive pressure during inspiration and a relatively lower pressure during expiration, all without interference with the spontaneous breathing of the patient. The described apparatus is operable to provide such treatment for sleep apnea or other patients by providing a flow of breathing gas to the patient at positive pressure, and varying the pressure of the air flow to provide alternatively high and low pressure within the airway of the patient coordinated with the patient's spontaneous inhalation and exhalation.

To provide pressure control, the flow rate of breathing gas to the patient is detected and processed to continually provide a signal which is proportional to the instantaneous flow rate signal is further processed to eliminate variations attributable to normal patient respiration and other causes thus generating a signal which is proportional to the average or steady state system gas flow. The average flow signal is continually compared with the instantaneous flow signal as a means to detect the state of the patient's spontaneous breathing versus average system flow. When instantaneous flow exceeds the average flow, the patient is inhaling, and in response the pressure of gas flowing to the patient is set at a selected positive pressure, to provide a corresponding positive pressure within the airway of the patient. When comparison of the instantaneous flow rate signal with the average flow signal indicates the patient is exhaling, as for example when the instantaneous flow signal indicates flow equal to or less than the average flow, the pressure of breathing gas to the patient is adjusted to a selected lower pressure to provide a corresponding lower pressure within the airway of the patient.

In an alternative embodiment as shown in FIGS. 2 and 3, the low pass filter 38 is replaced by an estimated leak computer which includes a low pass filter as well as other functional elements as shown in FIG. 3. The remainder of the system as shown in FIG. 2 is similar in most respects to the system shown in FIG. 1. Accordingly, like elements are identified by like numbers, and the description hereinabove of FIG. 1 embodiment also applies generally to FIG. 2.

By using the operative capability of the estimated leak computer 50, as described hereinbelow, it is possible to adjust the reference signal that is fed to decision circuitry 34 on a breath by breath basis rather than merely relying on long term average system flow. To distinguish this new reference signal from average system flow it will be referred to hereinbelow as the estimated leak flow rate signal or just the estimate leak signal.

As was noted hereinabove, the average system flow rate reference signal changes very slowly due to the long time constant of the low pass filter 38. This operative feature was intentionally incorporated to avoid disturbance of the reference signal by aberrant instantaneous flow rate signal incurred such as erratic breathing patterns. While it was possible to minimize the impact of such aberrations on the average flow rate reference signal, the average flow signal did nevertheless change, although by small increments and only very slowly in response to disturbances. Due to the long time constant of the low pass filter, such changes in the reference signal even if transitory could last for a long time.

Additionally, even a small change in the reference signal could produce a very significant effect on system triggering. For example, since the objective is to trigger the system to the IPAP mode when inhalation flow just begins to go positive, small changes in the reference signal could result in relatively large changes in the breathing effort needed to trigger the system to the IPAP mode. In some instances the change in reference signal could be so great that with normal breathing effort the patient would be unable to trigger the system. For example, if the system were turned on before placement of the mask on the face of the patient, the initial free flow of air from the unattached mask could result in a very large magnitude positive value for initial average system flow. If such value were to exceed the maximum inspiratory flow rate achieved in spontaneous respiration by the patient, the system would never trigger between the IPAP and EPAP modes because the decision circuitry would never see an instantaneous flow rate signal greater than the average flow rate signal, at least not until a sufficient number of normal breathing cycles after application of the mask to the patient to bring the reference signal down to a value more closely commensurate with the actual system leak in operation. As has been noted, with the low pass filter this could take a rather long time, during which time the patient would be breathing spontaneously against a uniform positive pressure. This would be tantamount to conventional CPAP and not at all in keeping with the present invention.

In addition to the embodiment based on a reference signal derived from estimated leak flow rate on a breath by breath basis which is controlled totally by spontaneous patient breathing, two further modes of operation also are possible, one being spontaneous timed operation in which the system automatically triggers to the IPAP mode for just long enough to initiate patient inspiration if the system does not sense inspiratory effort within a selected time after exhalation begins. To accomplish this, a timer is provided which is reset at the beginning of each patient inspiration whether the inspiratory cycle was triggered spontaneously or by the timer itself. Thus, only the start of inspiration is initiated by the timer. The rest of the operating cycle in this mode is controlled by spontaneous patient breathing and the circuitry of the system to be described.

A further mode of operation is based purely on timed operation of the system rather than on spontaneous patient breathing effort, but with the timed cycles coordinated to spontaneous patient breathing. The patient must do the coordination. The circuit timing is completely independent of patient.

Referring to FIG. 3, the estimated leak computer 50 includes the low pass filter 38' as well as other circuits which are operative to make corrections to the estimated leak flow rate signal based on on-going analysis of each patient breath. A further circuit is provided which is operative to adjust the estimated leak flow rate signal quickly after major changes in system flow such as when the blower has been running prior to the time when the mask is first put on the patient, or after a major leak the system has either started or has been shut off.

The low pass filter 38' also includes a data storage capability whose function will be described hereinbelow.

The low pass filter 38' operates substantially as described above with reference to FIG. 1 in that it provides a long term average of system flow which is commensurate with steady state system leakage including the flow capacity of the exhaust port 24. This long term average is operative in the FIG. 3 embodiment to adjust the estimated leak flow rate reference signal only when system flow conditions are changing very slowly.

To provide breath by breath analysis and adjustment of the reference signal, a differential amplifier 52 receives the instantaneous flow rate signal as indicated at 54, and the estimated leak signal output from low pass filter 38' as indicated at 56.

The output of differential amplifier 52 is the difference between instantaneous flow rate and estimated leak flow rate, or in other words estimated instantaneous patient flow rate 58. This will be clear upon considering the instantaneous flow is the sum of patient flow plus actual system leakage. The estimated patient flow signal output from differential amplifier 52 is provided, as indicated at 58, to a flow integrator 60 which integrates estimate patient flow breath by breath beginning and ending with the trigger to IPAP. Accordingly, an additional input to the flow integrator 60 is the IPAP/EPAP state signal as indicated at 62. The IPAP/EPAP state signal 42 is the same as the drive signal provided to pressure controller 26; that is, it is a signal indicating of the pressure state, as between IPAP and EPAP, of the system. The state signal thus may be used to mark the beginning and end of each breath for purposes of breath by breath integration by integrator 60.

If the estimated leak flow rate signal from low pass filter 38' is equal to the true system leak flow rate, and if the patient's inhaled and exhaled volumes are identical for a given breath (i.e. total positive patient flow equals total negative patient flow for a given breath), then the integral calculated by integrator 60 will be zero and no adjustment of estimated leak flow rate will result. When the integral calculated by integrator 60 is non-zero, the integral value in the form of an output signal from integrator 60 is provided, as indicated at 64, to a sample and hold module 66. Of course, even with a zero value integral, an output signal may be provided to module 66, but the ultimate result will be adjustment of the estimated leak flow rate signal.

A non-zero integral value provided to module 66 is further provided to module 38' as indicated at 68 with each patient breath by operative action of the IPAP/EPAP state signal upon module 66 as indicated at 70. The effect of a non-zero integral value and in the direction which would reduce the integral value towards zero on the next breath if all other conditions remain the same.

With this system, if the patient's net breathing cycle volume is zero, and if the system leak flow rate changes, the integrator circuit will compensate for the change in the leak flow rate by incremental adjustments to the estimated leak flow rate within about ten patient breaths.

The integrator circuit 60 also will adjust the estimated leak flow rate signal in response to no-zero net volume in a patient breathing cycle. It is not unusual for a patient's breathing volume to be non-zero. For example, a patient may inhale slightly more on each breath than he exhales over several breathing cycles, and then follow with a deeper or fuller exhalation. In this case, the integrator circuit would adjust the estimated leak flow rate signal as if the actual system leak rate had changed; however, since the reference signal correction is only about one tenth as large as would be required to make the total correction in one breath, the reference signal will not change appreciable over just one or two breaths. Thus, the integrator circuit accommodates both changes in system leakage and normal variations in patient breathing patters. The integrator circuit normally would be active, for example, during rapid patient breathing.

An end exhalation module 74 is operative to calculate another data component for use in estimating the system leak flow rate as follows. The module 74 monitors the slope of the instantaneous flow rate wave form. When the slope value is near zero during exhalation (as indicated by the state signal wave form remains small after more than one second into the respiratory phase, the indication is that exhalation has ended and that the net flow rate at this point thus is the leak flow rate. However, if estimated patient flow rate is non-zero at the same time, one component of the instantaneous flow rate signal must be patient flow. When these conditions are met, the circuit adjust the estimated leak flow rate slowly in a direction to move estimated patient flow rate toward zero to conform to instantaneous patient flow conditions expected at the end of exhalation. The adjustment to estimate leak flow rate is provided as an output from module 74 to low pass filter 38' as indicated at 80. When this control mechanism takes effect, it disables the breath by breath volume correction capability of integrator circuit 60 for that breath only.

The output of module 74 is a time constant control signal 42 which is provided to low pass filter 38' to temporarily shorten the time constant thereof for a sufficient period to allow the estimated leak flow rate to approach the instantaneous flow rate signal at that specific instant. It will be noted that shortening the low pass filter time constant increases the rapidity with which the low pass filter output (a system average) can adjust toward the instantaneous flow rate signal input.

Another component of estimated leak flow rate control is a gross error detector 82 which acts w hen the estimated patient flow rate, provided thereto as indicate at 84, is away from zero for more than about 5 seconds. Such a condition may normally occur, for example, when the flow generator 14 is running before mask 22 is applied to the patient. This part of the control system is operative to stabilize operation quickly after major changes in the leak rate occur.

In accordance with he above description, it will be seen that low pass filter 38' acts on the instantaneous flow rate signal to provide an output corresponding to average system flow, which is system leakage since patient inspiration and expiration over time constitutes a net positive flow of zero. With other enhancements, as described, the system average flow can be viewed as an estimate of leakage flow rate.

The differential amplifier 52 processes the instantaneous flow rate signal and the estimated leak flow rate signal to provide an estimated patient flow rate signal 58 which is integrated and non-zero values of the integral are fed back to module 38' to adjust the estimated leak flow rate signal 40 on a breath by breath basis. The integrator 60 is rest by the IPAP/EPAP state signal 42 via connection 62.

Two circuits are provided which can override the integrator circuit, including end exhalation detector 74 which provides an out put to adjust the time constant of low pass filter 38' and which also is provided as indicated at 86 to reset integrator 60. Gross error detector 82 is also provided to process estimated patient flow rate and to provide an adjustment to estimated leak flow rate under conditions as specified. The output of module 82 also is utilized as an integrator reset signal as indicated at 86. It will be noted that the integrator 60 is reset with each breath of the patient if, during that breath, it is ultimately overridden by module 74 or 82. Accordingly, the multiple reset capabilities for integrator 60 as described are required.

In operation, the system may be utilized in a spontaneous triggering mode, a spontaneous/timed mode or a purely timed mode or operation. In spontaneous operation, decision circuitry 34 continuously compares the instantaneous flow rate with estimated leak flow rate. If the system is in the EPAP state or mode, it remains there until instantaneous flow rate exceeds estimated leak flow rate by approximately 40 cc per second. When this transition occurs, decision circuitry 34 triggers the system into the IPAP mode for 150 milliseconds. The system will then normally remain the IPAP mode as the instantaneous flow rate to the patient will continue to increase during inhalation due to spontaneous patient effort and the assistance of the increased IPAP pressure.

After the transition to the IPAP mode in each breath, a temporary offset is added to the estimated leak flow rate reference signal. The offset is proportional to the integral of estimated patient flow rate beginning at initiation of the inspiratory breath so that it gradually increases with time during inspiration at a rate proportional to the patient's inspiratory flow rate. Accordingly, the flow rate level above estimated leak flow needed to keep the system in the IPAP mode during inhalation decreases with time from the beginning of inhalation and in proportion to the inspiratory flow rate. With this enhancement, the longer an inhalation cycle continues, the larger is the reference signal below which instantaneous flow would have to decrease in order to trigger the EPAP mode. For example, if a patient inhales at a constant 500 cc per second until near the end of inspiration, a transition to EPAP will occur when his flow rate drops to about 167 cc per second after one second, or 333 cc per second after two seconds, or 500 cc per second after three seconds, and so forth. For a patient inhaling at a constant 250 cc per second, the triggers would occur at 83, 167 and 250 cc per second at one, two and three seconds into IPAP, respectively.

In this way, the EPAP trigger threshold comes up to meet the inspiratory flow rate with the following benefits. First it becomes easier and easier to end the inspiration cycle with increasing time into the cycle. Second, if a leak develops which causes an increase instantaneous flow sufficient to trigger the system into the IPAP mode, this system will automatically trigger back to the EPAP mode after about 3.0 seconds regardless of patient breathing effort. This would allow the volume-based leak correction circuit (i.e. integrator 60) to act as if it is activated with each transition to the IPAP mode. Thus, if a leak develops suddenly, there will be a tendency toward automatic triggering rather than spontaneous operation for a few breaths, but the circuit will not be locked into the IPAP mode.

Upon switching back to the EPAP mode, the trigger threshold will remain above the estimated leak flow rate for approximately 500 milliseconds to allow the system to remain stable in the EPAP mode without switching again while the respective flow rates are changing. After 500 milliseconds, the trigger threshold offset is reset to zero to await the next inspiratory effort.

The normal state for the circuit is for it to remain in the EPAP mode until an inspiratory effort is made by the patient. The automatic corrections and adjustments to the reference signal are effective to keep the system from locking up in the IPAP mode and to prevent auto-triggering while at the same time providing a high level of sensitivity to inspiratory effort and rapid adjustment for changing leak conditions and breathing patterns.

In the spontaneous/timed mode of operation, the system performs exactly as above described with reference to spontaneous operation, except that it allows selection of a minimum breathing rate to be superimposed upon the spontaneous operating mode. If the patient does not make an inspiratory effort within a predetermined time, the system will automatically trigger to the IPAP mode for 200 milliseconds. The increased airway pressure for this 200 milliseconds will initiate patient inspiration and provide sufficient time that spontaneous patient flow will exceed the reference signal so that the rest of the cycle may continue in the spontaneous mode as above described. The breaths per minute timer is reset by each trigger to IPAP whether the transition was triggered by the patient or by the timer itself.

In the timed operating mode, all triggering between IPAP and EPAP modes is controlled by a timer with a breath per minute control being used to select a desired breathing rate from, for example, 3 to 30 breaths per minute. If feasible, the selected breathing rate is coordinated to the patient's spontaneous breathing rate. The percent IPAP control is used to set the fraction of each breathing cycle to be spent in the IPAP mode. For example, if the breaths per minute control is set to 10 breaths per minute (6 seconds per breath) and the percent IPAP control is set to 33%, then the flow generator will spend, in each breathing cycle, two seconds in IPAP and four seconds in EPAP.

The disclosure now turns to discussion of an arrangement, according to at least one preferred embodiment of the present invention, that can be utilized in the general framework of an apparatus such as that described and illustrated with respect to FIGS. 1–3 or in other contexts, including those discussed in the "Background" section of this disclosure and/or as set forth in any of the U.S. patents cited therein.

Figure 4:
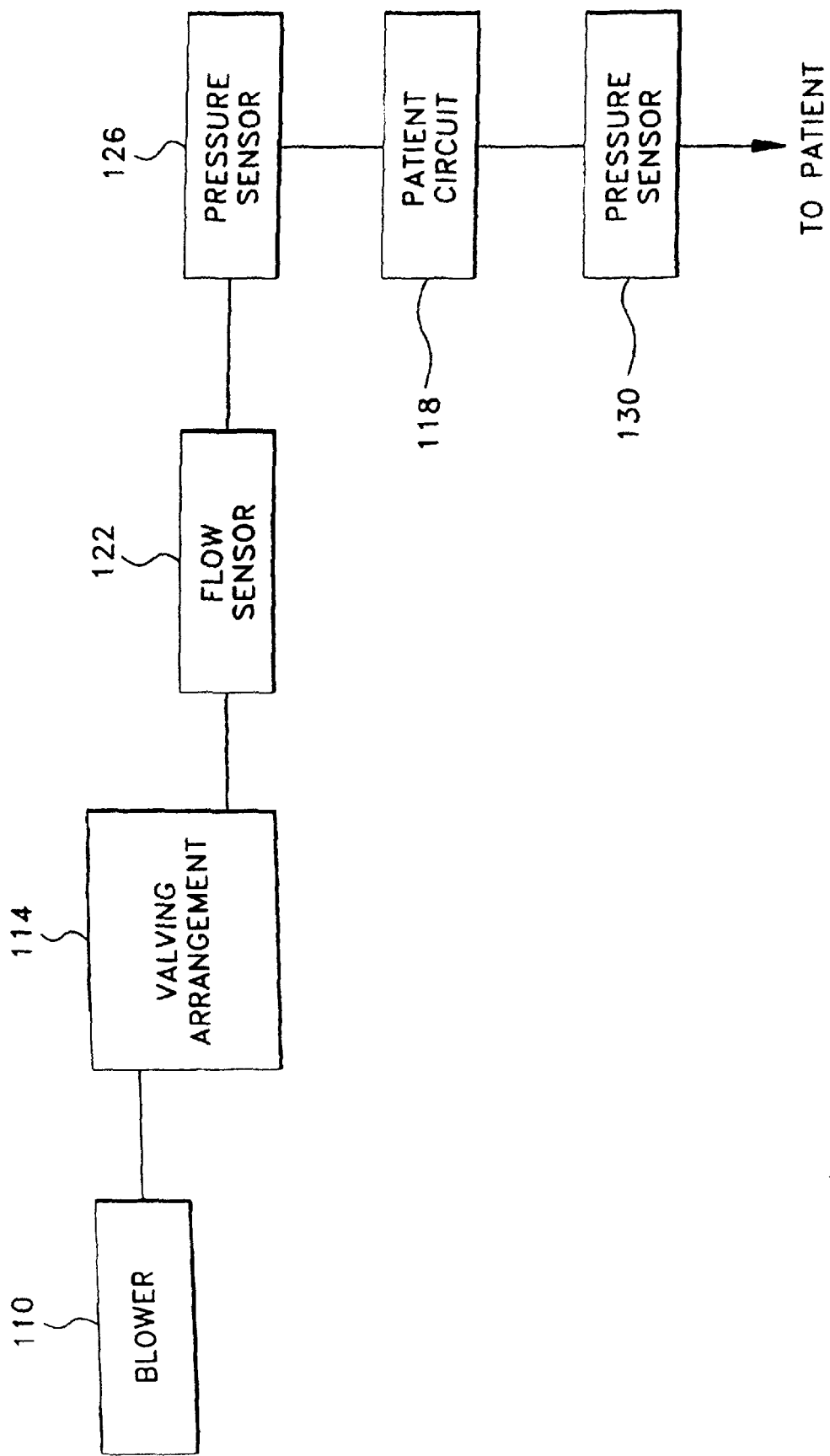
FIG. 4 schematically illustrates components of a respirator circuit according to at least one preferred embodiment of the present invention.

In FIG. 4, there is schematically illustrated a blower 110 connected to a valving arrangement 114 designed in accordance with at least one embodiment of the present invention. Generally, such blowers are well-known to those of ordinary skill in the art and will not be discussed in further detail herein. Also illustrated in FIG. 4 is a patient circuit 118, a concept which would also appear to be well-known to those of ordinary skill in the art. Indicated at 122, 126 and 130, respectively, are suitable devices for measuring flow rate, "outlet pressure" (i.e., the pressure present in the air stream prior to entering the patient circuit) and the "patient pressure" (i.e., the pressure present in the air stream prior to the same being directed to the patient's mask so as to be inhaled by the patient).

Figure 5:
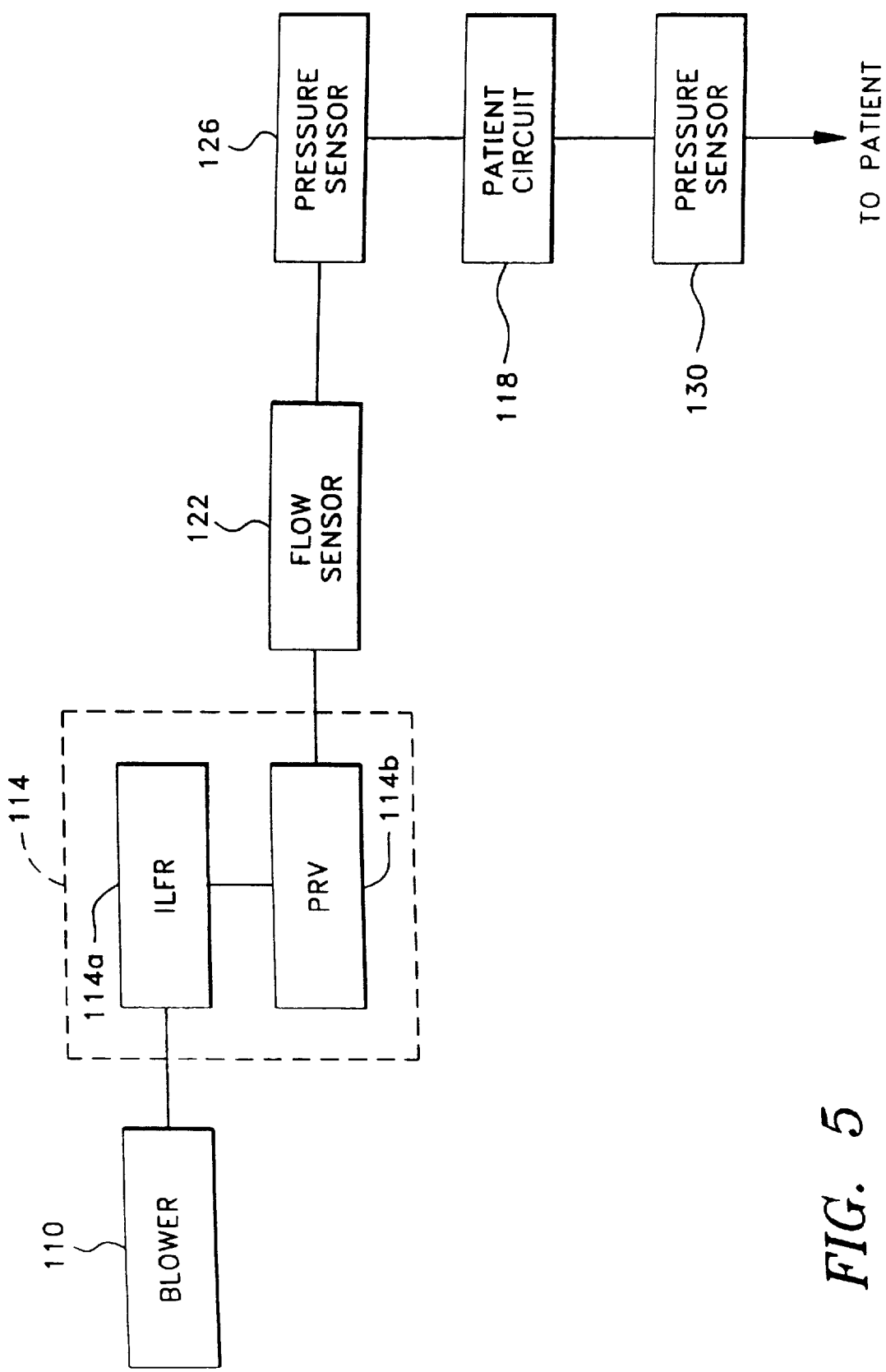
FIG. 5 also schematically illustrates components of a respirator circuit according to at least one preferred embodiment of the present invention.

FIG. 5 illustrates, in accordance with at least one preferred embodiment of the present invention, the provision of two valves 114a and 114b as the aforementioned valving arrangement 114. For the purpose of further discussion, valve 114a, shown as being the valve situated more closely in fluid communication with blower 110, may be termed the "in-line flow restrictor" or the "ILFR" valve, while the valve 114b situated downstream from valve 114a may be termed a "pressure relief valve" or "PRV".

In accordance with a preferred embodiment of the present invention, ILFR 114a will be so configured as to provide a means for restricting flow in the respirator circuit without venting any flow to the ambient atmosphere or other remote location. In contrast, PRV 114b will preferably be configured to operate in the manner of a conventional pressure relief valve, such that it will serve to vent flow to the ambient atmosphere or other selected remote location.

Accordingly, ILFR 114a and PRV 114b will preferably be provided and configured in a manner deemed suitable for the context at hand and, in this sense, can conceivably each be embodied by any arrangements suitable for carrying out their respective above-discussed tasks. A more specific embodiment, however, will be discussed further below.

Figure 5A:
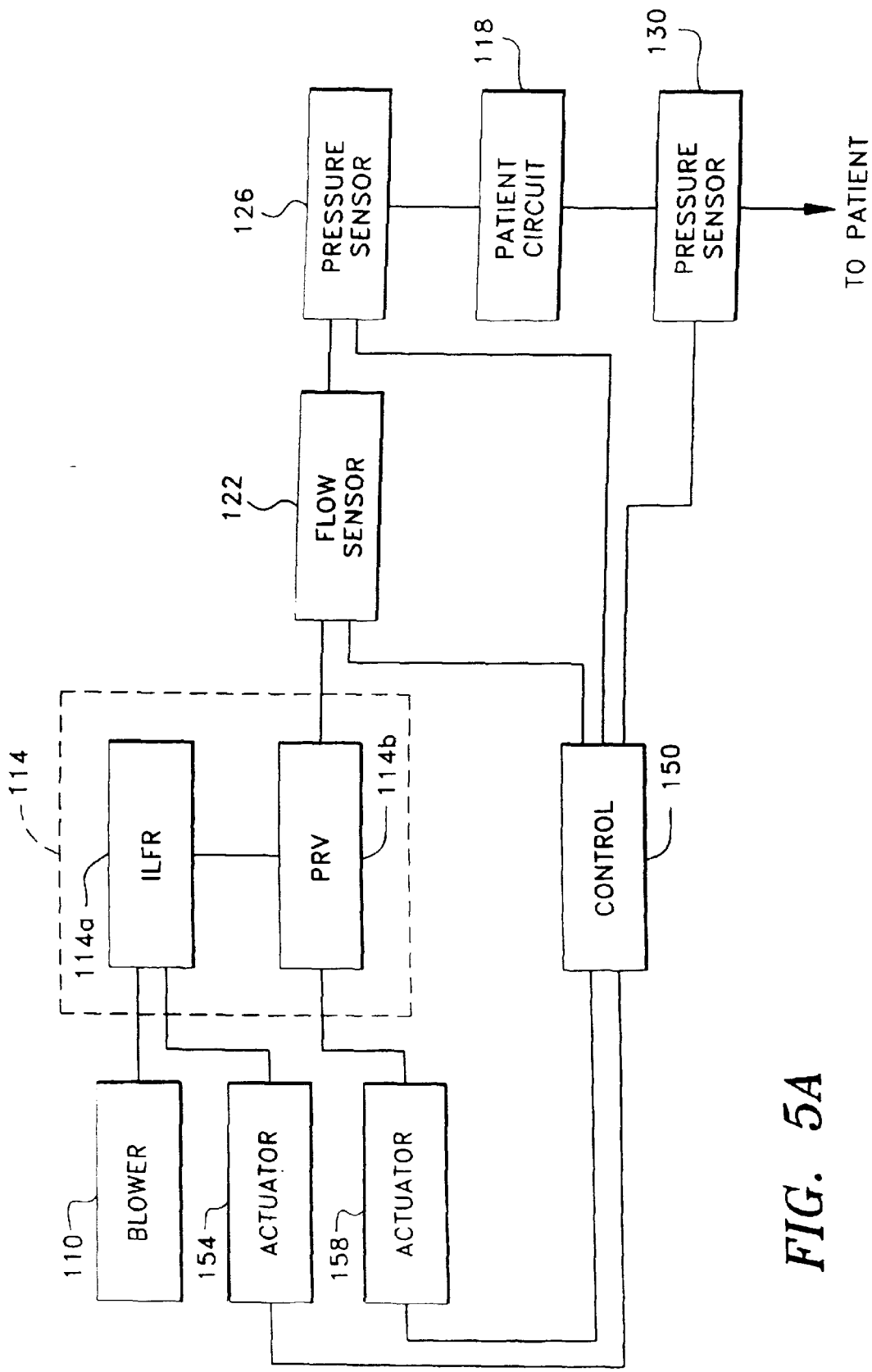
FIG. 5A schematically illustrates essentially the same components as shown in FIG. 5, but also schematically illustrates a control system.

FIG. 5A schematically illustrates the inclusion of a control arrangement 150 which, in accordance with a preferred embodiment of the present invention, may monitor any or all of flow sensor 122, pressure sensor 126 and pressure sensor 130, and, in a manner deemed suitable for the operation at hand, prompt suitable actuators 154 and 158 to respectively activate ILFR 114a and/or PRV 114b so as to control pressure and/or flow to the patient.

As an example, in the context of a "BiPAP" procedure, it may first be assumed that a predetermined "IPAP" pressure (that is, a constant pressure to be administered to the patient during inhalation) is preselected at a suitable console, thereby prompting blower 110 to output at a given motor speed for a given resultant initial "deadhead" pressure. Already, control 150 may preferably prompt ILFR 114a and PRV 114b to each be actuated to respective degrees so as to preferably provide the desired target IPAP pressure to the patient (conceivably as measured by sensor 130) while minimizing the flow that is vented by PRV 114b.

In this respect, it may now be appreciated that ILFR 114a and PRV 114b are each preferably embodied by proportional-type valving schemes that can be essentially continuously adjustable. In the case of ILFR 114a, for example, maximum "closure" of the valve could result in maximally constricted flow, while minimum closure (or maximal "opening") could result in minimally constricted flow. On the other hand, PRV 114b may be embodied in the manner of a conventional pressure relief valve, that is, it will preferably open to varying degrees so as to exhaust varying degrees of flow away from the respirator circuit. Types of proportional valves suitable for these purposes, as well as suitable actuators, would appear to be well-known, and will thus not be further discussed at present. For example it is conceivable to employ in each case a poppet-type valve that is selectively and proportionally actuable by way of a variable electrical current applied to the respective actuator.

The manner of respectively controlling ILFR 114a and PRV 114b will preferably be carried out so as to fulfill the objectives of adequately providing the pressure demanded for or by the patient while minimizing wasted flow that would otherwise be vented through a valve such as pressure relief valve 114b. In this respect, ILFR 114a and PRV 114b can preferably work in tandem, a scenario that can be easily programmed into the control arrangement 150.

Whereas a single pressure relief valve, such as that indicated at 114b, might normally require being open to a significant degree most of the time in order to permit a margin of safety in the event that a high level of air or gas pressure is demanded for or by the patient (as discussed previously in the "Background" section of this disclosure), so as to close to a given degree to increase flow and pressure upon such a demand, it may now be appreciated that ILFR 114a can essentially preclude the need for such extensive "preliminary" opening of the PRV 114b. More particularly, the ILFR 114a can serve to restrict flow and pressure initially, essentially with a similar effect as a conventional pressure relief valve as just described but without the added disadvantage that flow is unnecessarily vented away from the respirator circuit.

It will be appreciated that the possible schemes of operation of an ILFR 114a and PRV 114b according to the present invention cover a wide range, all with the effect of minimizing wasted flow in comparison with previous single pressure-relief valve systems. In one embodiment, the PRV 114b may initially be open to a given degree so as to vent flow during times when excess pressure is not demanded. Simultaneously, ILFR 114a may be closed to a given degree (i.e. in a position to restrict flow to a given degree) during such times. Depending on the control scheme adopted, it is conceivable to adjust either or both of the ILFR 114a and the PRV 114b when a demand for increased pressure is detected or prompted. In one embodiment of the present invention, this could be accomplished by continually opening the ILFR 114a while allowing the PRV 114b to remain at the same position as previously. Consequently, if the ILFR 114a were to open to a maximal degree in the presence of a particularly acute pressure demand, the PRV 114b could be prompted to "kick in" and subsequently close so as to augment the added pressure and flow provided by the maximal opening of the ILFR 114a. Alternatively, a reverse scenario could take place, in which pressure regulation during "normal" periods (i.e. during periods in which not acutely high pressure levels are demanded by or for the patient) could be effected by the PRV 114b, followed by augmentation by the ILFR 114a when needed. Either alternative may conceivably be chosen with a view to accomplishing any particularly desired objectives (for example, the latter alternative scenario could be adopted if the venting of excess flow is not seen as detrimental and if, for example, the accumulation of back-pressure in the blower is desired to be prevented).

Upon an exhalation by the patient, by using appropriate sensors and circuitry such as that described with reference to FIGS. 1–3, it is conceivable to exact a situation in which the ILFR 114a will maximally close and the PRV 114b will maximally open, so as to permit the exhaled air or gas, now travelling back through the respirator circuit in the direction towards blower 110, to be vented away through PRV 114b.

Figure 6:
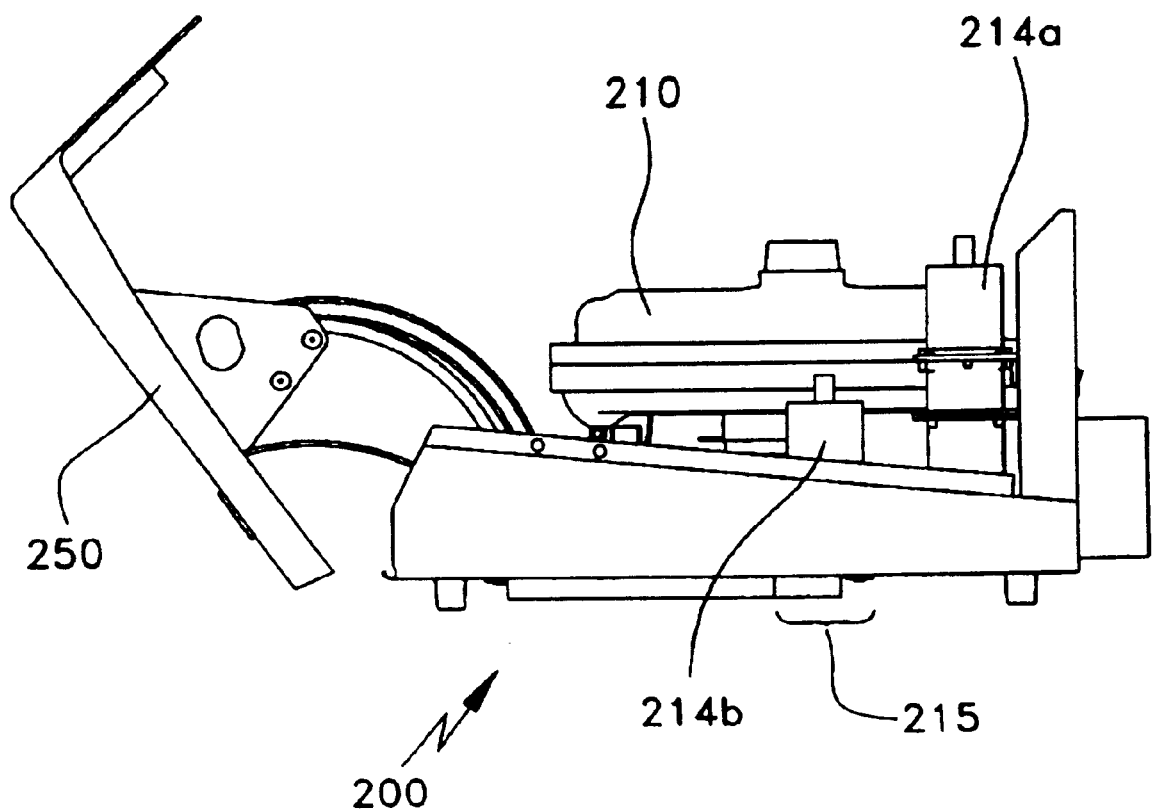
FIG. 6 is an elevational view of main portion of a respiration device according to an embodiment of the present invention.
Figure 7:
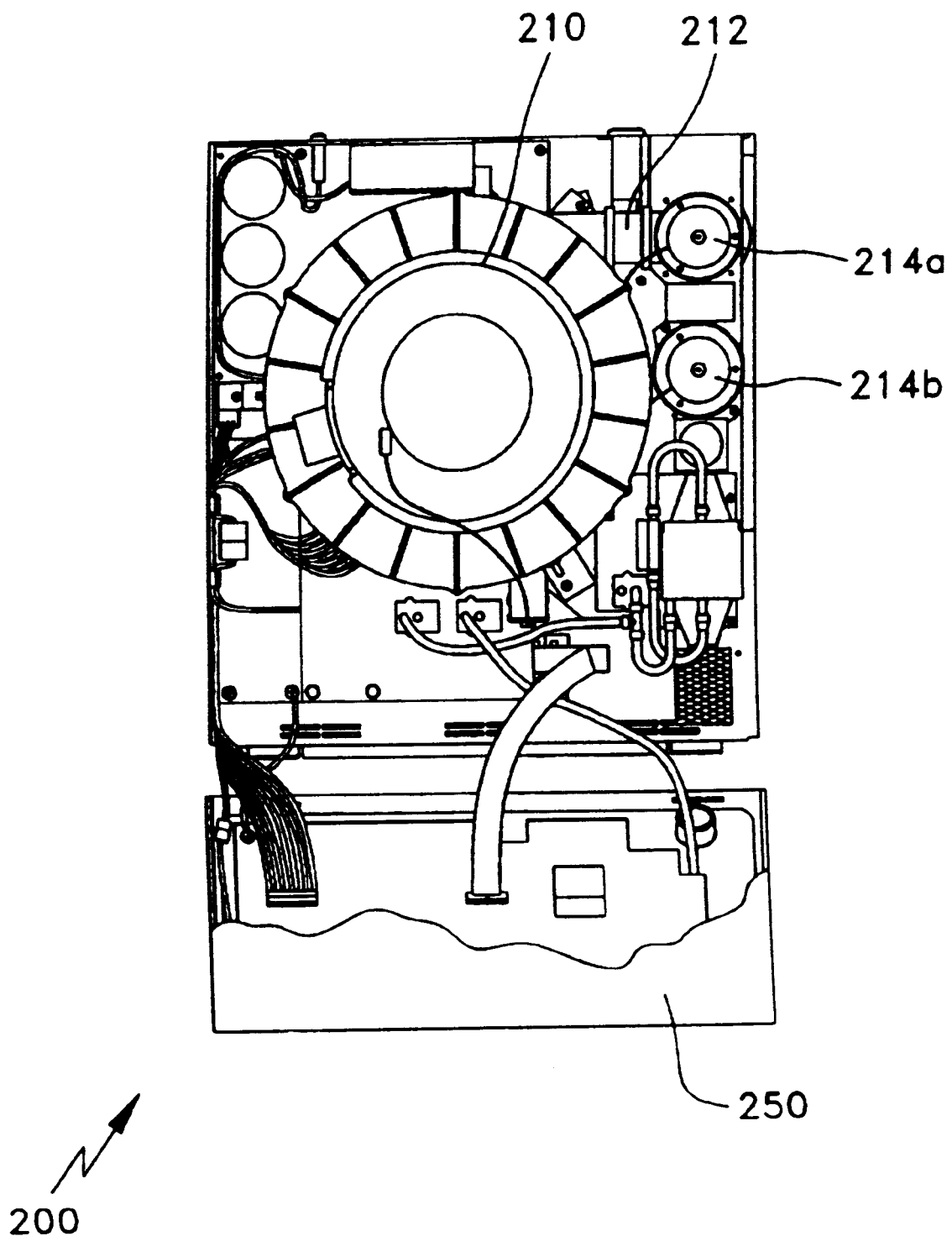
FIG. 7 is a plan view of the respiration device illustrated in FIG. 6.

FIGS. 6 and 7 illustrate a general layout of a respiration apparatus 200 that may be employed in accordance with the embodiments of the present invention. Particularly, a suitable conduit 212 may preferably lead from blower 210 into ILFR 214a, which in turn will direct flow to PRV 214b. As shown in FIG. 6, a region 215 underneath PRV 214b may preferably serve as the region from which flow is exhausted or bled out of the apparatus 200 into the ambient atmosphere. Also shown in FIGS. 6 and 7 is a removable cover 250.

Figure 8:
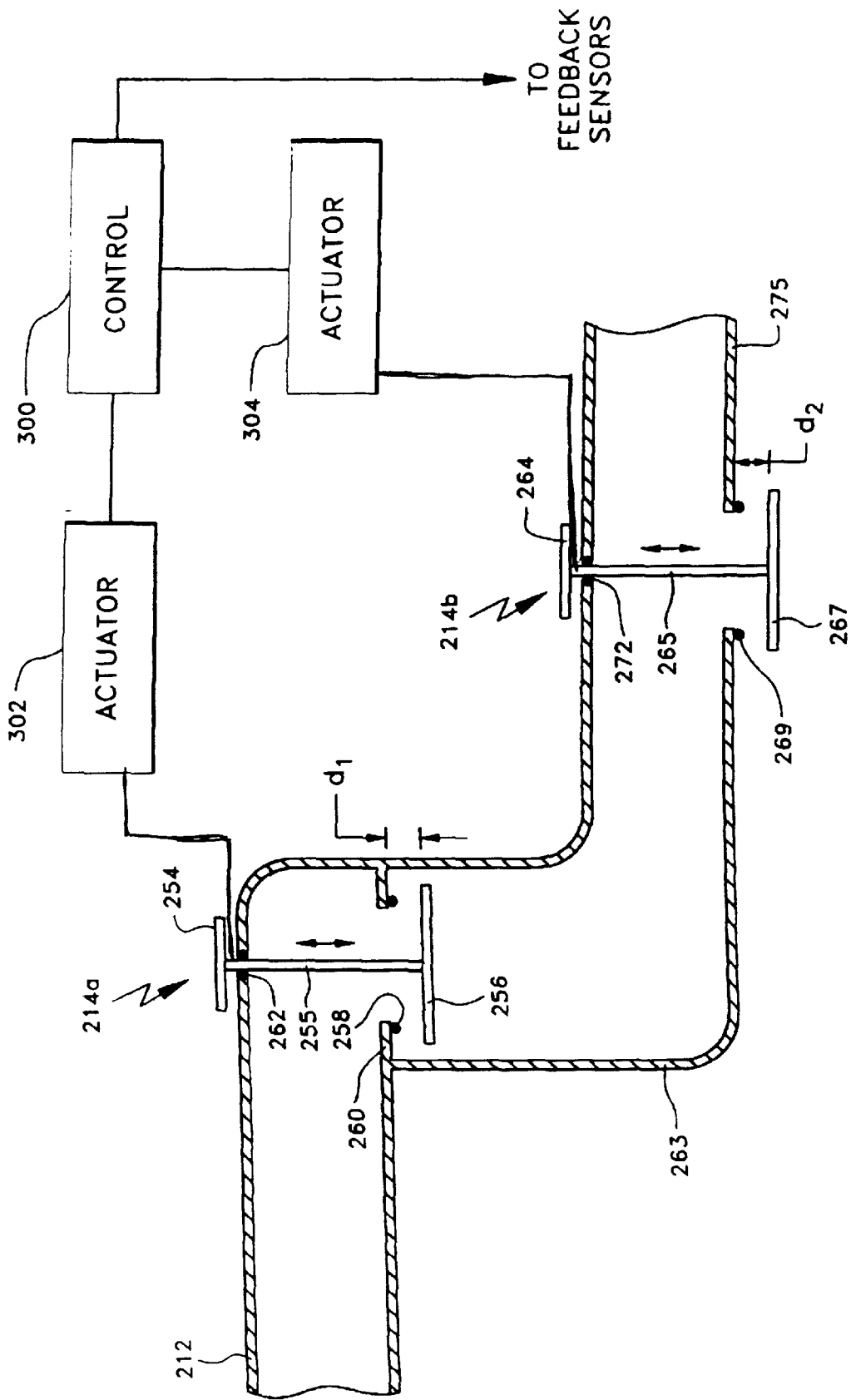
FIG. 8 is a detailed illustration of a valving arrangement according to an embodiment of the present invention.

FIG. 8 shows a more detailed illustration of valving arrangements 214a and 214b that may be employed in accordance with the present invention.

Preferably, ILFR 214a may include a head portion 254, a rod portion 255 and a piston or disc portion 256. As illustrated, conduit 212 may preferably lead towards ILFR 214a in such a manner that, with piston/disc portion 256 displaced maximally upward, such that it rests against suitably configured and oriented stop or stops 258, flow from the blower will be maximally restricted at this point. With piston/disc portion 256 displaced maximally downward, flow from the blower will be minimally restricted. Preferably, a suitable sealing arrangement 262 may be provided about rod portion 255 at its region of interaction with conduit 212.

To achieve maximal opening of ILFR 214a, it is conceivable to permit the striking of head 254 against the exterior of conduit 212 to serve as a limit position. Alternatively, it is conceivable to provide, within conduit 263 (i.e. that conduit portion that extends downwardly from ILFR 214a), suitable stops that will cease downward movement of piston/disc 256 at a predetermined position.

Preferably, even with ILFR 214a maximally closed, there will preferably be a provision for some minimal degree of flow to progress past ILFR 214a. Thus, in one embodiment of the present invention, there could be provided a given number of stops 258, spaced circumferentially at given distances from one another, that would still permit a minimal degree of flow with piston/disc portion 256 in a maximally upward position. Alternatively, piston/disc portion 256 could be embodied by a slotted disc that would permit such minimal flow. Other arrangements, including other types of stops provided in the interior of conduit 263, are certainly conceivable within the scope of the present invention.

Conduit portion 263 may preferably lead from ILFR 214a to PRV 214b, which itself may include a head portion 264, a rod portion 265 and a piston or disc portion 267. As illustrated, with piston/disc portion 267 displaced maximally upward, such that it rests against suitably configured and oriented stop or stops 269, flow will be minimally vented (with a concomitant increased pressure). Further, with piston/disc portion 267 displaced maximally downward, flow will be maximally vented (with a concomitant reduced pressure). Preferably, a suitable sealing arrangement 262 may be provided about rod portion 255 at its region of interaction with conduit 212.

With the provision of a control arrangement 300, itself linked to system feedback sensors of the type described and alluded to variously throughout this disclosure, and also of suitable actuators 302 and 304 (respectively dedicated to ILFR 214a and PRV 214b), it will be appreciated that respective opening distances $d_1$ and $d_2$ of ILFR 214a and PRV 214b can be controlled to achieve the inventive pressure and flow regulation discussed heretofore.

Herebelow, a brief discussion is provided of one possible mode of operation according to a preferred embodiment of the present invention.

Naturally, at the outset of a procedure in which a patient is to utilize a respiration device according to the present invention, he or she will first put on a mask that has been provided. For the present discussion, it can be assumed that the mask will represent part of a "non-invasive" treatment, in which the patient does not accept any respirator components internally.

With the respiratory device being turned on, in accordance with at least one preferred embodiment of the present invention, either the patient or clinician may then establish the "IPAP" and "EPAP" levels discussed and alluded to hereinabove if a "bi-level" apparatus is being used. Alternatively, if an apparatus is being used that employs a more variable scheme of pressure provision, the patient or clinician will either activate a stored program that expressly varies pressures over time or possibly activate a scheme that depends on instantaneous patient monitoring. Subsequently, the patient or clinician may actually activate the respiration process by utilizing an appropriate switch for starting the blower 110.

The patient will then inhale, and in view of the sensing circuitry described hereinabove, the machine will be alerted to provide the appropriate pressure to the patient. Inasmuch as the base or "static" flow now provided by the blower 110 will necessarily be augmented by the patient's inward breath, the effective flow rate of air or gas through the patient's mask into the patient's airway will represent an increase over the initial flow level provided by the blower.

As discussed hereinabove, it would have been typical, in the past, for any excess flow to be vented at any one of a number of suitable points along the respiration circuit.

"Excess flow", in this context, is the difference between the required blower circuit flow (required to produce the commanded patient circuit pressure) and the actual flow taken in by the patient. However, in accordance with at least one preferred embodiment of the present invention, the ILFR 114a, with the aid of the aforementioned feedback circuitry, will preferably be adjusted in such a manner as to restrict flow from the blower itself and, if necessary, concomitantly alter the blower output so as to still provide the desired IPAP pressure. Of course, during this time, the PRV 114b may also be controllably linked with the ILFR 114a by way of a control arrangement such as those discussed heretofore. Thus, by the time the air flow reaches the patient, the target pressure will be present with only minimal wasted flow.

Upon completion of an inhalation breath, and at the outset of an exhalation breath by the patient, the sensing circuitry described and alluded to hereinabove will appropriately alert the control circuitry into providing another pressure, possibly a so-called EPAP pressure. At this point, in accordance with at least one preferred embodiment of the present invention, essentially two actions may be effected. First, the ILFR will preferably close as much as possible (although it is conceivable to maintain a minimum opening with the ILFR 114a, possibly by utilizing mechanical stops or the like). In so doing, it will help prepare for the next stage, in which the patient's exhaled breath will return through the respiration circuit up to the PRV 114b. In a known manner, the PRV 114b will be opened in such a manner as to permit the patient's returning breath to be exhausted to the ambient atmosphere or to another predetermined location. At this point, the ILFR 114a will be used for the purpose of controlling pressure while minimizing flow from the blower, a condition that can easily be programmed into the control circuitry.

Once the patient's exhalation breath is complete and he or she then begins a new inhalation breath, the process described hereinabove will again be repeated, wherein a pressure such as an "IPAP" pressure will again be effected by blower 110. Possibly, ILFR 114a will be continuously adjusted, in response to pressures demanded by the patient, until such a time that demand is so acute that the negligibly opened PRV 114b will close, to increase pressure.

It will be appreciated that a valving arrangement according to the present invention will be capable of accommodating significantly high pressure and flow, even in the presence of a highly restrictive patient circuit 118. It has been found that valving arrangements, such as the combination of ILFR 114a and PRV 114b disclosed herein, are capable of controlling a deadhead pressure of 60 cm $H_2O$ or higher.

The disclosure now turns to a discussion of an oxygen mixing arrangement according to at least one preferred embodiment of the present invention, as illustrated in FIGS. 9–15.

Figure 9:
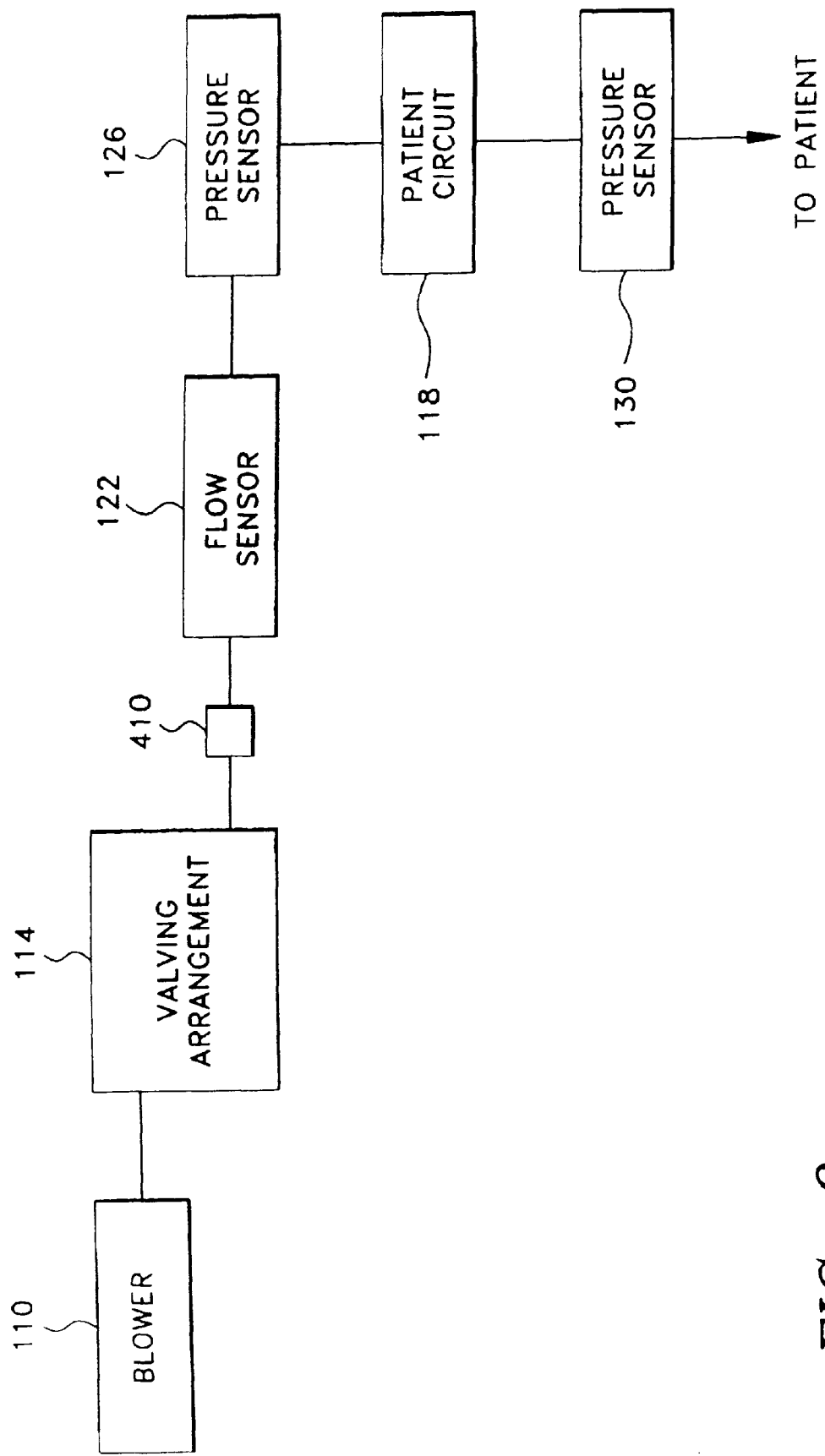
FIG. 9 schematically illustrates components of a respiratory circuit according to at least one preferred embodiment of the present invention, and includes a junction point suitable for receiving an oxygen module according to at least one preferred embodiment of the present invention.

FIG. 9 illustrates a general pressure support respiration arrangement similar to that described and illustrated hereinabove with respect to FIG. 4, with the addition of a junction 410 that is provided between valving arrangement 114 and patient circuit 118. Further, in FIG. 9, junction 410 is shown as being positioned between valving arrangement 114 and flow sensor 122.

In accordance with a preferred embodiment of the present invention, junction 410 will preferably be so configured and arranged so as to accommodate a selectively insertable oxygen module, as will be discussed herebelow. Preferably, junction 410 may take the form of a "tee" junction or the like, examples of which would appear to be well-known of ordinary skill in the art.

Figure 10:
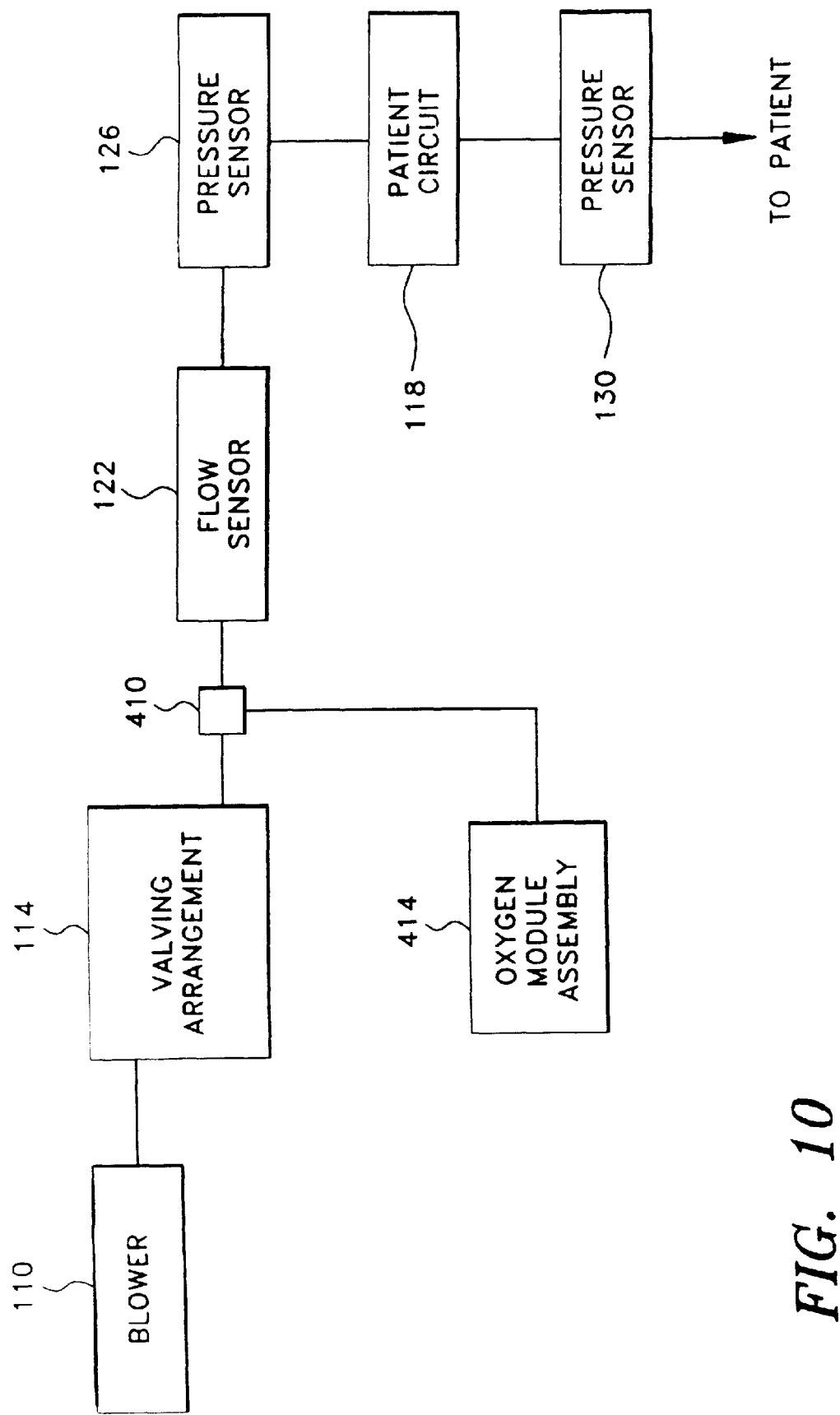
FIG. 10 is essentially the same schematic illustration as FIG. 9, but additionally illustrates the inclusion of an oxygen module according to at least one preferred embodiment of the present invention.

FIG. 10 illustrates, in schematic form, the addition of an oxygen module to the arrangement shown in FIG. 9. Particularly, an oxygen module 414 may be selectively connectable into the greater apparatus illustrated in FIG. 9 by way of the aforementioned junction 410.

Figure 10A:
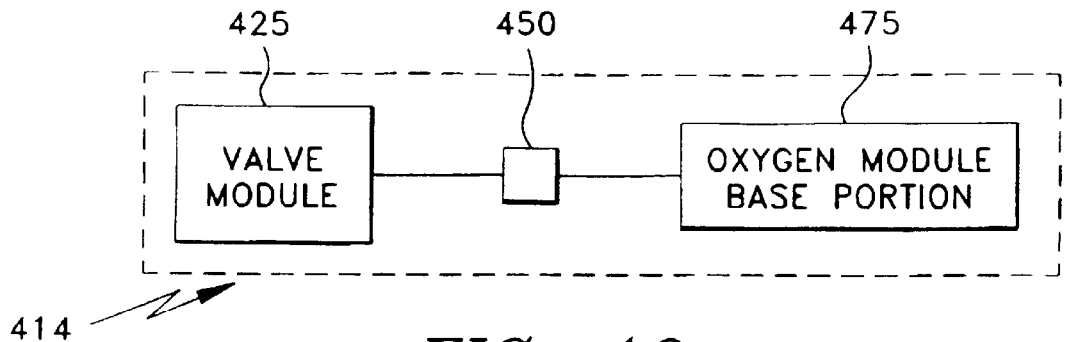
FIG. 10A schematically illustrates components of an oxygen module according to at least one preferred embodiment of the present invention.

FIG. 10A illustrates the composition of oxygen module 414 according to a preferred embodiment of the present invention. Particularly, as shown in FIG. 10A, oxygen module 414 may include a valve module 425, an oxygen module base portion 475 and a connecting arrangement 450 for connecting and disconnecting valve module 425 and base portion 475 with respect to one another.

Figure 10B:
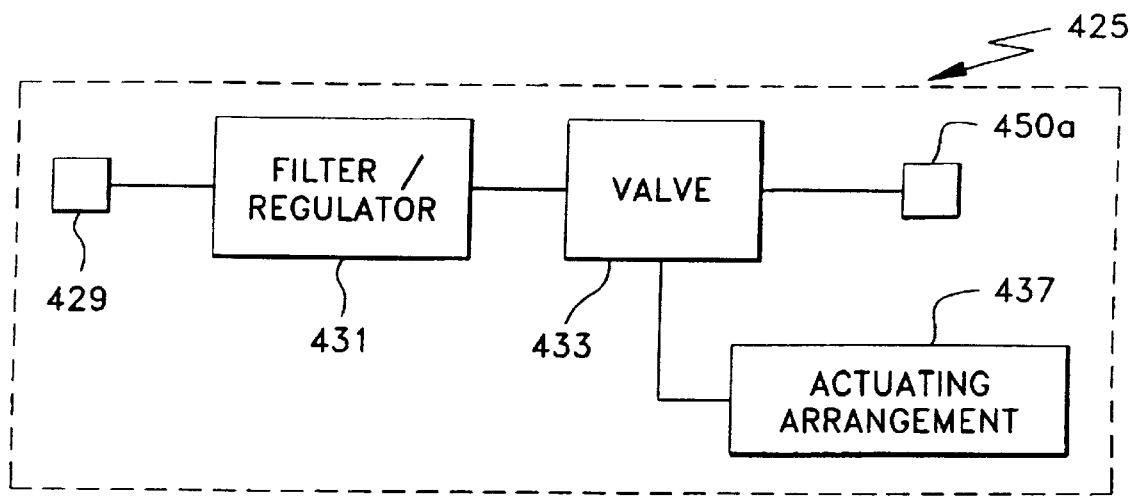
FIGS. 10B and 10C schematically illustrate, in more detail, subsidiary components of the components shown in FIG. 10A.

FIG. 10B more particularly illustrates, in schematic form, the aforementioned valve module 425. As shown in FIG. 10B, valve module 425 may preferably include a connection arrangement 429 for accepting oxygen from an external source (such as a gas bottle or a hospital gas supply system), a filter/regulator 431, valving 433 for controlling the flow of oxygen (and its subsequent level of concentration in a greater respiration apparatus, and an exit connection arrangement 450a.

Also illustrated schematically in FIG. 10B is an actuating arrangement 437 that will preferably form part of the valve module 425 and will also be so configured and arranged as to adequately control the valving 433 for the purposes discussed herein.

As an example, connection arrangement 429 could be embodied by the well-known "DISS" standard oxygen fitting capable of being connected to hospital gas supplies (such as oxygen supply outlets contained in walls near hospital patient beds).

The valving 433 could be embodied, for example, by a number of small, off-the-shelf, normally-closed spring-return poppet valves (driven by a solenoid) such as those manufactured by Pneutronics, Inc. (a division of Parker-Hannifan). If it is to be assumed, as an example, that each valve will provide approximately 35 L/min. (liters per minute) of flow at 35 psi (pounds per square inch) drive pressure, in one embodiment of the present invention, three such valves could be employed. Preferably, the valves may be wired such that driving control for the valves can be applied simultaneously to each valve. The aforementioned Pneutronics valves have been found to be particularly advantageous, as they are designed to open at a precise current level, thereby circumventing the problem of control non-linearities associated with an arrangement in which all valves do not open simultaneously.

Preferably, filter/regulator 431 may be so configured and arranged as to preclude the type of accumulation of particles (e.g. via patient exhalation) in the valving 433 of valve module 425 that might otherwise cause the valving to stick open and permit oxygen leakage. Preferably, filter/regulator 431 may be so configured and arranged as to throttle down the drive pressure (of the oxygen being supplied onward to a respirator apparatus) to a desirably low level, such as 50 psi, to reduce the variability of inadvertent design variations (such as those that might initiate from manufacture) that could otherwise have an effect on supply pressure or controllability of the valve actuator plant. Suitable filter/regulators are also known to be manufactured by Parker-Hannifan, including "bowl"-type filter/regulators illustrated in FIGS. 12 and 13.

Figure 10C:
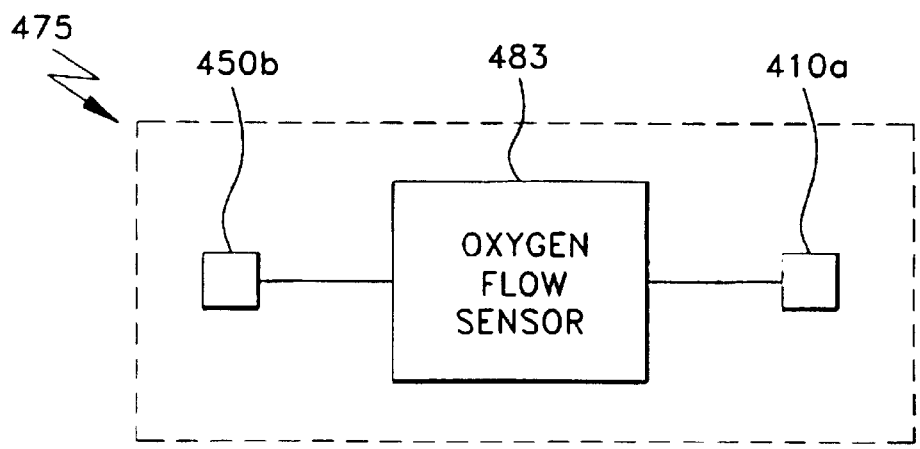

As shown schematically in FIG. 10C, an oxygen module base portion 475, in accordance with a preferred embodiment of the present invention, may include an inlet connection arrangement 450b (to interface with the aforementioned exit connection arrangement 450a of a valve module 425) and an oxygen flow sensor 483. Downstream from flow sensor 483, a connection arrangement 410a will also preferably be provided, and may be so configured and arranged as to be integrable with a connection arrangement such as that indicated at 410 in FIG. 9.

The oxygen flow sensor 483 could preferably include a sensor calibration table and associated control electronics.

Of course, it is to be understood that the specific incarnations of connection arrangement 429, valving 433, filter/regulator 431 and flow sensor 483, as discussed hereinabove, are provided only as examples and are in no way meant to limit the scope of the present invention. In this respect, it will be appreciated that essentially any suitable connection arrangements, valving arrangements, filtering/regulation arrangements and/or sensing arrangements may be used in the context of the present invention for the purpose of carrying out the functions discussed herein.

Figure 11:
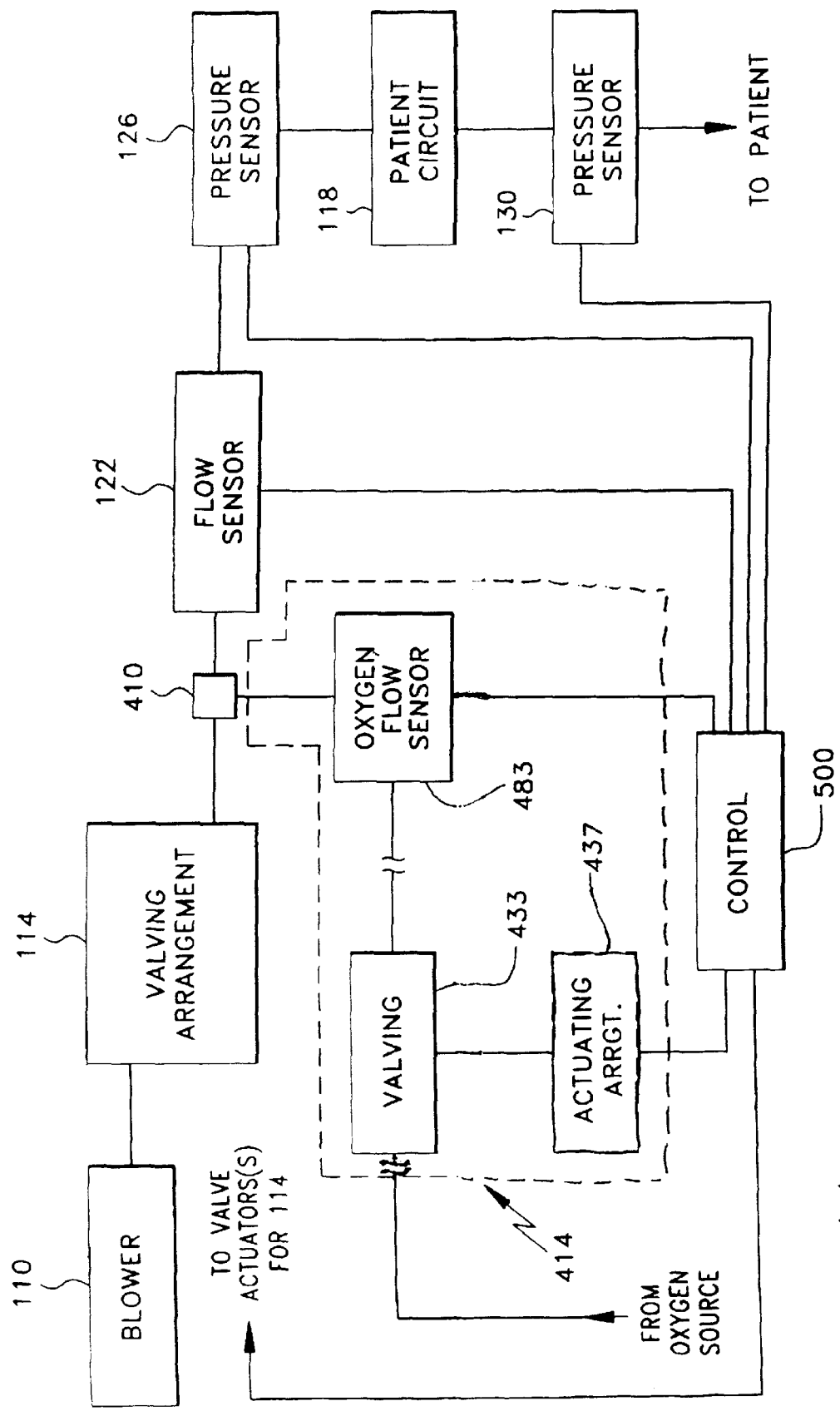
FIG. 11 schematically illustrates essentially the same components as shown in FIG. 10, but also schematically illustrates a control system.

FIG. 11 schematically illustrates the integration of oxygen module 414 into the general control scheme of an apparatus according to the present invention. Similar to the arrangement shown in FIG. 5A, a control system or control arrangement 500 may be so configured and disposed as to receive input from various sensors, such as flow sensor 22, pressure sensors 122 and 126, and oxygen flow sensor 483.

Accordingly, control 500 may, in accordance with at preferred embodiment of the present invention, be so configured and arranged so as to control the valving 433 of oxygen module 414 (conceivably via the aforementioned actuating arrangement 437) in a manner to be described in more detail further below. Of course, control system 500 will also preferably be configured to control valving arrangement 114 in substantially the same manner as described hereinabove with reference to FIGS. 4–8 or in any other manner deemed suitable for the application in question (with the possible exception of adjustments made in view of oxygen module 414, as will be discussed in more detail herebelow).

Thus, in accordance with a preferred embodiment of the present invention, control arrangement 500 may be configured for simultaneously controlling all valving arrangements in the system, including general valving arrangement 114 and oxygen module valving arrangement 433. Further, control arrangement 500 may preferably be specifically configured to control each valving arrangement in response only to given inputs. Thus, for example, in accordance with a preferred embodiment of the present invention, control 500 will be configured to control oxygen module valving 433 on the basis of inputs received from oxygen flow sensor 483 and general flow sensor 122. Likewise, general valving arrangement 114 may be controlled generally in the manner described and illustrated herein with respect to FIGS. 4–8, but can also be controlled on the basis of inputs received from oxygen flow sensor 483. A more detailed description of a possible control scheme according to the present invention is provided further below.

It is to be noted that, although a single control arrangement 500 is illustrated in FIG. 11, it is conceivable, in accordance with one embodiment of the present invention, to provide two separate control arrangements, one of which would be designated for controlling oxygen module valving 433 and the other of which would be designated for controlling general valving arrangement 114. Alternatively, a single control arrangement 500 could still be provided, which would however be effectively "divided" between the two designated tasks of controlling oxygen module valving 433 and controlling general valving arrangement 114. In either case, each dedicated control arrangement (or portion of a control arrangement) would only receive inputs from that sensor (or those sensors) specifically relevant for the designated task of that control arrangement (or portion of a control arrangement). Thus, for example, in the case of a dedicated control arrangement (or portion of a control arrangement) for controlling oxygen module valving 433, in one embodiment of the present invention, only inputs from a general flow sensor (such as that indicated at 122) and an oxygen flow sensor (such as that indicated at 483) would be received.

It may now be appreciated, with reference to FIGS. 9–11 that, in accordance with a preferred embodiment of the present invention, the connection arrangement 410 of a greater respiration apparatus will preferably accommodate an oxygen module 414 at a point of the respiration circuit that is downstream from any pressure-controlling valving arrangement 114 (i.e. between such a valving arrangement 114 and the patient circuit 118). In the context of an arrangement such as that shown in FIG. 5 (i.e. with an in-line flow restrictor 114a and a pressure relief valve 114b), the connection 410 for accommodating oxygen module 414 will preferably be placed between pressure relief valve 114b and patient circuit 118.

Accordingly, as long as the net flow of air and/or gas in the ventilator is towards the patient and away from the blower, it will be appreciated that all oxygen injected into the general respirator circuit at connection 410 will go only to the patient circuit and not towards any pressure-relieving valves that might otherwise vent oxygen away from the system. On the other hand, control 500 could preferably be configured so as to automatically shut off all oxygen supply from oxygen module 410 upon a net flow of zero or less being detected (i.e. in instances where there is no positive net flow towards the patient as discussed above). In this manner, even in the presence of net exhaust flow back from the patient circuit 118 towards valving 114, the risk of any oxygen (other than that residing in, and having the potential to leak from, the patient circuit) being inadvertently vented away to the ambient atmosphere, under any circumstances, will be virtually eliminated.

Figure 12:
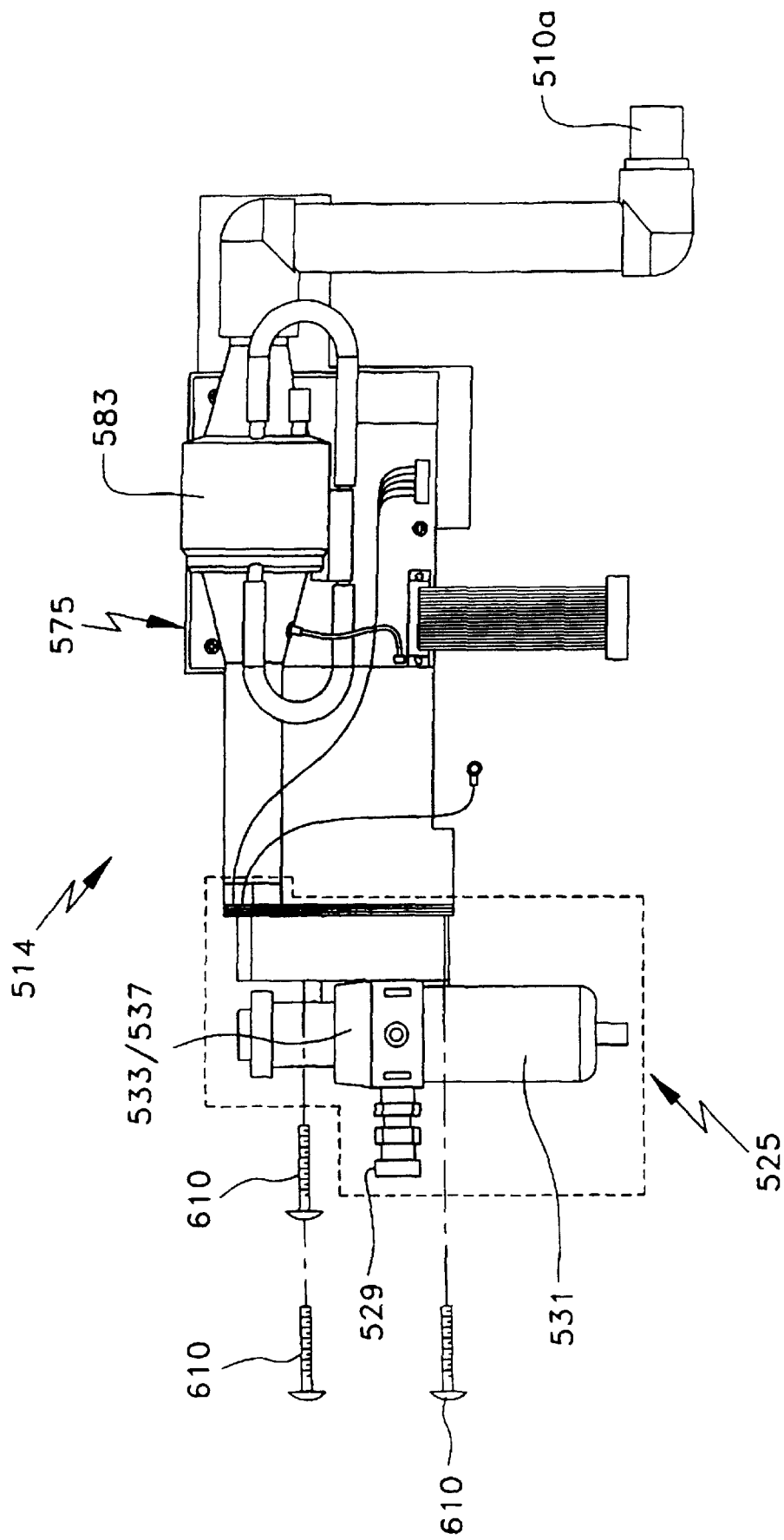
FIGS. 12 and 13 respectively provide different elevational views of a modular oxygen-providing unit.

FIG. 12 illustrates a layout of an oxygen module arrangement 514 that may be employed in accordance with the embodiments of the present invention. Particularly, a valve module 525 is shown that may be integrable with an oxygen module base portion 575.

As shown, inlet port 529 (connectable to an oxygen supply) may lead into filter/regulator 531 and valving 533 (with constituent actuating arrangement 537). Preferably mounted at oxygen module base portion 575 is oxygen flow sensor 583. From oxygen flow sensor 583, a suitable conduit will preferably lead to a connection 510a that can be selectively inserted into a suitably configured receptor connection in a general respiration apparatus (such as a "tee" connection in a general respiration apparatus).

A suitable connection medium, such as screws or bolts 610, may be used to selectively integrate valve module 525 and base portion 575 with one another. Additionally, this same connection medium 610 could be used to secure valve module 525 onto the exterior of a respiration apparatus.

Figure 13:
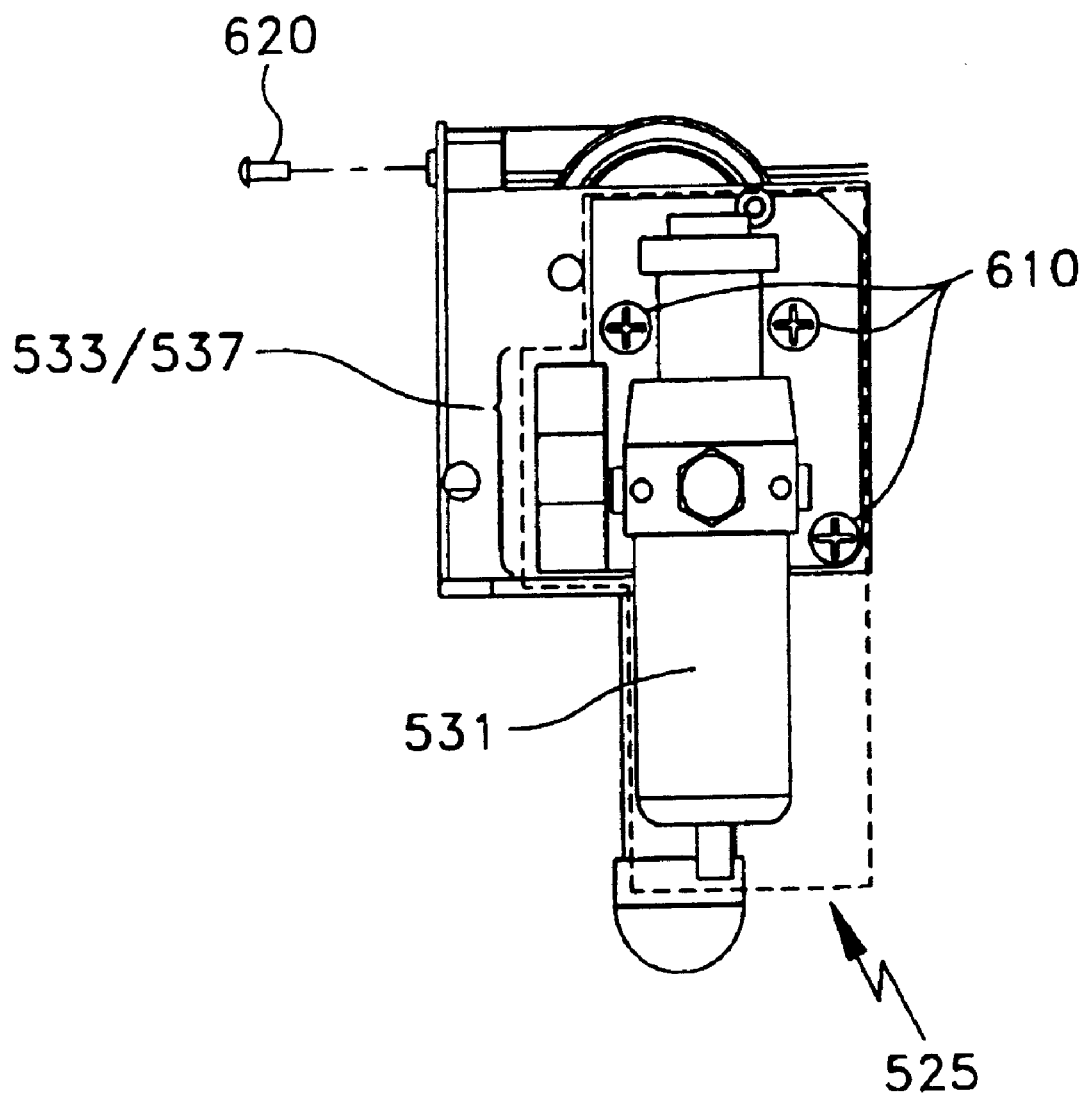

FIG. 13 shows an orthogonally distinct side view of valve module 525 with respect to the view shown in FIG. 12, and additionally illustrates a connection medium 620 (such as screws, rivets, bolts or the like) that could be used to secure either or both of valve module 525 and base portion 575 with respect to a greater respiration apparatus.

Figure 14:
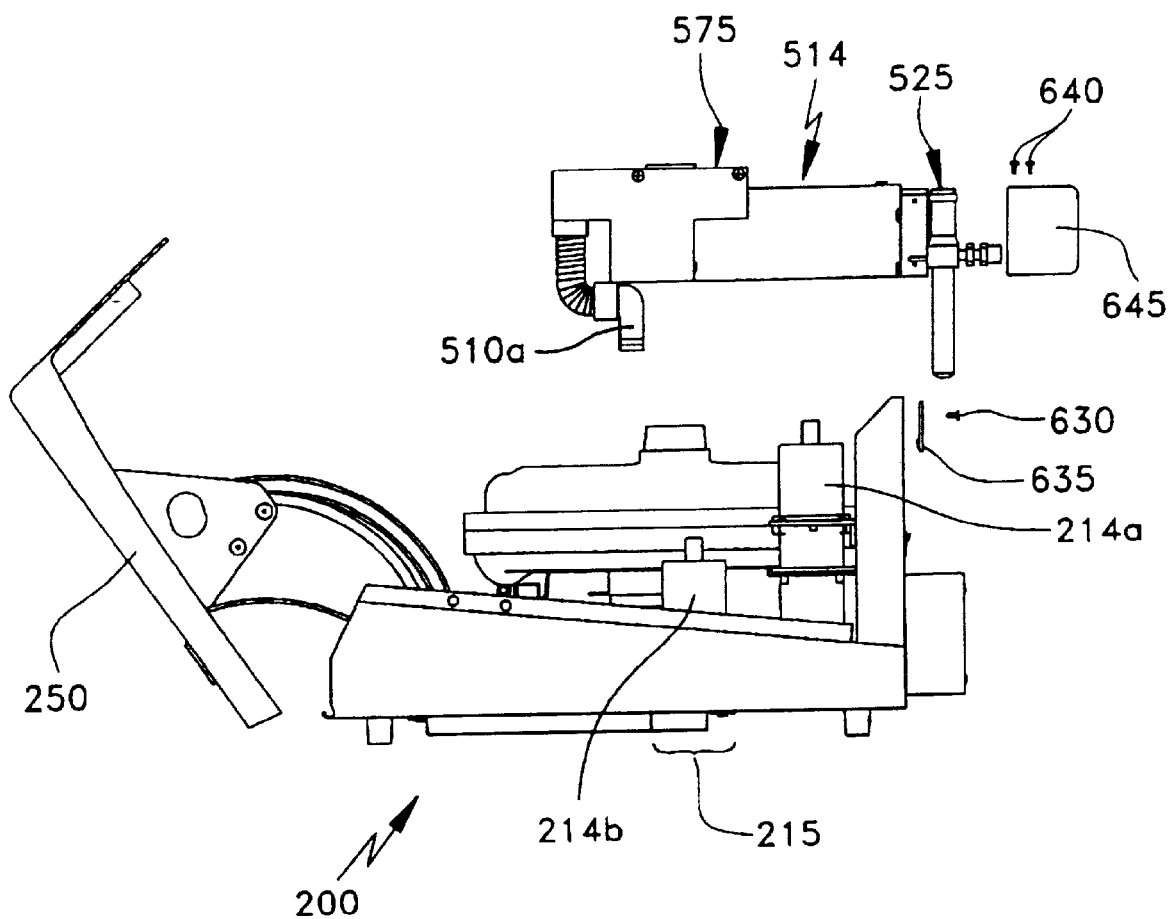
FIG. 14 is an elevation view of a main portion of a respiration device according to an embodiment of the present invention shown in exploded view along with a modular oxygen-producing device.

In FIG. 14, a general respiration apparatus 200 similar to that illustrated in FIG. 6 is shown. It is to be understood that the type of respiration apparatus illustrated in FIG. 14 is provided only as an example of a context for the integration of an oxygen module 514 into a greater system, and is in no way meant to be restrictive. (For example, although FIG. 14 illustrates an ILFR 214a and PRV 214b similar to that described and illustrated with respect to FIG. 6, it should be understood that this is only one example of a system into which an oxygen module 514 according to the present invention can be integrated.)

In addition to the components already described with respect to FIG. 6, an oxygen module 514 according to an embodiment of the present invention is also shown, separate from the greater respiration apparatus 200. As shown, connection 510a may extend in such a manner as to be readily integrable with a suitable receptor connection within apparatus 200.

Figure 15:
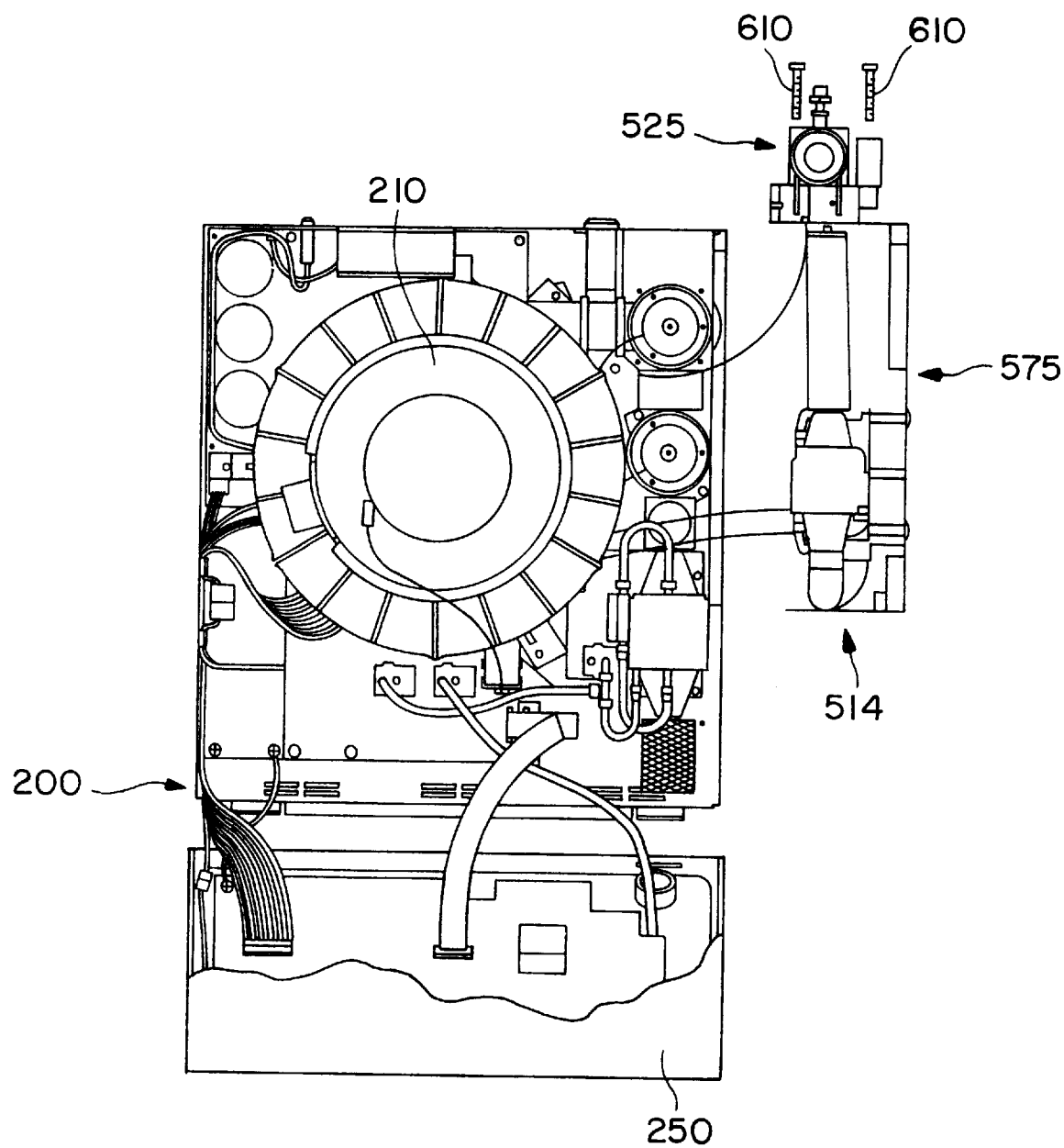
FIG. 15 is a plan view of the ensemble arrangement illustrated in FIG. 14.

FIG. 15 shows a plan view of the arrangement shown in FIG. 14, and again illustrates connecting media 610 than may be used to secure valve module 525 onto base portion 575 and/or apparatus 200.

With reference to FIGS. 12–15, in accordance with a preferred embodiment of the present invention, valve module 525, including filter/regulator 531 and valving 533 (with constituent actuating arrangement 537) will be so configured and arranged as to actually reside on the outside of apparatus 200 upon integration of module 514 with apparatus 200, while base portion 575 can preferably reside on the inside of apparatus 200. Preferably, a cover 645 (securable via suitable screws, bolts or rivets 640) will be provided so as to shield the valving 533 and actuating arrangement 537 of valve module 525. A plate 635, with attendant connection media 630, may also be provided to facilitate the connection of valve module 525 on the outside of apparatus 200. Preferably, no access to valving 533 and actuating arrangement 537 will be possible without removal of cover 645 (whereas access to filter/regulator 531 will still preferably be possible).

It will be appreciated that, in accordance with at least one preferred embodiment of the present invention, an oxygen module 514, including both base portion 575 and valve module 525, can be selectively integrable with one or more respirator apparatus, on different occasions, as needed. It is also conceivable, by rendering valve module 525 and base portion 575 selectively integrable and separable from one another, to permit the interchanging of one valve module 525 for another at a given point in time, without necessitating the concomitant replacement of base portion 575. Thus, the present invention contemplates, in accordance with at least one preferred embodiment, a system of interchangeable parts that could preclude the frequent replacement of entire oxygen module systems as well as a modular arrangement for providing oxygen that can be integrated into a large number of different general respiration apparatus (such as pressure support ventilators).

The disclosure now turns to a brief discussion of pressure control, as well as the control of oxygen concentration, in accordance with at least one preferred embodiment of the present invention.

Preferably, essentially any suitable algorithm may be chosen for the purpose of injecting a predetermined concentration (and flowrate) of oxygen into an airstream emanating from a general respirator apparatus. It has been found that an apparatus according to the present invention will generally be capable of providing, to a patient, an overall oxygen concentration of between about 21% (i.e. atmospheric concentration) to about 100%.

In one embodiment of the present invention, such control can be maintained via appropriate feedback sensors and control arrangements such as those discussed heretofore. In a particularly advantageous refinement of the present invention, the flowrate of oxygen (for example, as injected into the general respirator apparatus airstream at connection 410 as shown in FIG. 10) that is necessary for maintaining a predetermined concentration of oxygen administered to the patient, can be governed by the overall airstream flowrate as measured by an appropriate sensor or sensors (such as the flow sensor 122 illustrated in FIG. 11). In this manner, as the overall flowrate fluctuates, the flowrate of oxygen into the general respirator airstream (as ultimately controlled, for example, by the actuating arrangement 437 and valving 433 schematically illustrated in FIG. 11) can rise and fall accordingly. In accordance with one preferred embodiment of the present invention, this may be accomplished by a linearly proportional "pegging" of the oxygen flowrate to the overall system flowrate (given a constant oxygen concentration). Additionally, further control of the oxygen flowrate can of course be governed by prompts from an appropriate feedback sensing arrangement, such as the oxygen flow sensor 483 schematically illustrated in FIG. 11.

In accordance with a preferred embodiment of the present invention, and especially in the context of a 2-valve pressure control system such as that described and illustrated with respect to FIGS. 4–8, it has been found that particular advantages of accurate oxygen flow control and overall patient pressure control are enjoyed if the oxygen flow control valving (such as the valving 433 illustrated schematically in FIG. 11) has a considerably faster response time, such as one order of magnitude faster, than the pressure control valving found in the general respirator circuit (such as the ILFR 114a and PRV 114b described and illustrated with respect to FIG. 5). The commercially-available valves discussed heretofore (i.e. the Pneutronics, Inc., valves) have been found to be particularly useful for this purpose.

Preferably, in accordance with at least one preferred embodiment of the present invention, all components in the airstream of the general respirator apparatus, as well as the oxygen module, will have flammability ratings compatible for contact with pure oxygen. Additionally, it is also preferably the case that all materials which can come in contact with oxygen will be rated not to undergo accelerated deterioration in its presence.

In accordance with a preferred embodiment of the present invention, in order to prevent the flow of patient circuit dead space oxygen from contacting high temperature surfaces, a sealed exit path may be provided to the atmosphere for returning gas. Preferably, the outlet of this port will not reside near a cooling fan inlet opening, so as to prevent the exhaust from being drawn back into the ventilator.

If not otherwise stated herein, it may be assumed that all components and/or processes described heretofore may, if appropriate, be considered to be interchangeable with similar components and/or processes disclosed elsewhere in the specification, unless an indication is made to the contrary.

It should be appreciated that the apparatus and methods of the present invention may be configured and conducted as appropriate for the application. The embodiments described above are to be considered in all respects only as illustrative and not restrictive. The scope of the invention is defined by the following claims rather than by the foregoing description. All changes which come within the meaning and range of equivalency of the claims are to be embraced within their scope.

What is claimed is:

1. An apparatus for delivering pressurized gas to an airway of a patient, said apparatus comprising:

gas flow generating means for providing a gas flow;

a primary conduit operatively coupled to said gas flow generating means to communicate said gas flow to an airway of a patient; and means for providing supplemental gas concomitantly with said gas flow that includes:
a supplemental conduit adapted to carry a flow of said supplemental gas,
a coupling member joining one end of said supplemental conduit and said primary conduit at a first location generally downstream of said gas flow generating means for introducing said flow of said supplemental gas into said primary conduit at said first location, and
regulating means for controlling said flow of said supplemental gas from said supplemental conduit to said primary conduit such that said flow of said supplemental gas from said supplemental conduit to said primary conduit is enabled responsive to a net flow of gas in said primary conduit at said first location being in a direction generally away from said gas generating means, and such that said flow of said supplemental gas from said supplemental conduit to said primary conduit is disabled responsive to said net flow of gas in said primary conduit at said first location being in a direction other than away from said gas generating means.

2. The apparatus according to claim 1, wherein said supplemental gas includes oxygen.

3. The apparatus according to claim 1, wherein said means for providing supplemental gas includes means for selecting a concentration of said supplemental gas to be delivered to said primary conduit, and wherein said regulating means continually adjusts said flow of said supplemental gas into said primary conduit so as to provide said selected concentration of said supplemental gas to a patient.

4. The apparatus according to claim 1, wherein said regulating means advances said flow of said supplemental gas at a rate that is directly proportional to said magnitude of said gas flow in said primary conduit.

5. The apparatus according to claim 1, wherein said means for providing supplemental gas comprises a modular section selectively attachable and detachable with respect to a remainder of said apparatus.

6. The apparatus according to claim 5, wherein said modular section comprises at least two modular sub-sections, each being selectively attachable and detachable with respect to one another.

7. The apparatus according to claim 6, wherein one of said modular sub-sections comprises said regulating means and another one of said modular sub-sections comprises said means for introducing supplemental gas into said conduit means.

8. An apparatus for delivering pressurized gas to an airway of a patient, said apparatus comprising:

gas flow generating means for providing a gas flow;

means for providing supplemental gas concomitantly with said gas flow that includes regulating means for controlling a flow of said supplemental gas as a function of at least one of a magnitude of said gas flow and a direction of said gas flow;

conduit means, operatively coupled to said gas flow generating means, for delivering said gas flow to an airway of a patient, pressure control means associated with one of said gas flow generating means and said conduit means for controlling a pressure of said gas flow in said conduit means;

venting means associated with said conduit means for selectively venting gas from said conduit means;

directing means associated with said conduit means for directing at least a portion of said gas flow in said conduit means through said venting means responsive to an exhalation by a patient; and preventing means associated with said means for providing supplemental gas for preventing a direct transfer of said supplemental gas to said venting means.

9. The apparatus according to claim 8, wherein said preventing means includes means for substantially blocking said flow of said supplemental gas into said conduit means responsive to detection of one of net airflow from a patient and a zero flow in said conduit means.

10. A method of delivering pressurized gas to an airway of a patient, comprising:

providing a primary gas flow to a patient via a gas flow generator;

carrying said primary gas flow to such a patient in a primary conduit providing a supplemental gas flow introducing said supplemental gas flow into said primary conduit at a first location in said primary conduit generally downstream of said gas flow generator;

enabling said supplemental gas flow to flow into said primary conduit responsive to a net flow of gas in said primary conduit at said first location being in a direction generally away from said gas generator; and disabling said supplemental gas flow from flowing into said primary conduit responsive to said net flow of gas in said primary conduit at said first location being in a direction other away from said gas generator.

11. The method according to claim 10, wherein said supplements gas includes oxygen.

12. An apparatus for delivering pressurized gas to an airway of a patient, said apparatus comprising:

a gas flow generator that provides a primary gas flow;

a primary conduit operatively coupled to said gas flow generator and adapted to provide said primary gas flow to a patient;

a sensor operatively coupled to said primary conduit to detect a rate of said primary gas flow in said primary conduit and to output a flow signal indicative thereof a supplemental conduit adapted to carry a supplemental gas flow;

a coupling member joining one end of said supplemental conduit to said primary conduit at a first location generally downstream of said gas flow generator for introducing said supplemental gas flow into said primary conduit at said first location;

a valve operatively coupled to said supplemental conduit to control said flow of supplemental gas therein, wherein said valve is actuated responsive to a supplemental gas flow control signal;

a processor operatively coupled to said sensor and said valve, wherein said processor determines a net flow of gas in said primary conduit at said first location based on said flow signal from said sensor, wherein said processor causes said valve to open allowing said supplemental gas flow to enter said primary conduit at said first location responsive to said net flow of gas in said primary conduit at said first location being in a direction generally away from said gas flow generator, and wherein said processor causes said valve to close preventing said supplemental gas flow from entering said primary conduit responsive to said net flow of gas in said primary conduit at said first location being in a direction other away from said gas flow generator.

* * * * *